US008815950B2

(12) United States Patent
Remenar et al.

(10) Patent No.: US 8,815,950 B2
(45) Date of Patent: Aug. 26, 2014

(54) PHARMACEUTICAL COMPOSITIONS AND METHOD OF USING LEVODOPA AND CARBIDOPA

(75) Inventors: Julius Remenar, Framingham, MA (US); Orn Almarsson, Shrewsbury, MA (US); Anthony J. Meehan, Jr., Shrewsbury, MA (US); Zhong Zhang, Sudbury, MA (US)

(73) Assignee: Janssen Biotech, Inc., Horsham, PA (US)

( * ) Notice: Subject to any disclaimer, the term of this patent is extended or adjusted under 35 U.S.C. 154(b) by 1223 days.

(21) Appl. No.: 11/083,168

(22) Filed: Mar. 17, 2005

(65) Prior Publication Data

US 2005/0203185 A1    Sep. 15, 2005

Related U.S. Application Data

(63) Continuation-in-part of application No. 10/926,702, filed on Aug. 26, 2004, now abandoned, and a continuation-in-part of application No. PCT/US2004/027607, filed on Aug. 26, 2004.

(60) Provisional application No. 60/586,442, filed on Jul. 8, 2004, provisional application No. 60/559,864, filed on Apr. 6, 2004, provisional application No. 60/505,551, filed on Sep. 24, 2003, provisional application No. 60/499,256, filed on Aug. 29, 2003.

(51) Int. Cl.
*A61K 31/197* (2006.01)

(52) U.S. Cl.
USPC ........................... 514/567; 514/565; 514/970

(58) Field of Classification Search
None
See application file for complete search history.

(56) References Cited

U.S. PATENT DOCUMENTS

| | | | |
|---|---|---|---|
| 3,928,431 | A | 12/1975 | Broderman et al. |
| 4,826,875 | A | 5/1989 | Chiesi |
| 5,017,607 | A | 5/1991 | Chiesi |
| 5,190,763 | A | 3/1993 | Edgren et al. |
| 5,525,631 | A | 6/1996 | Milman et al. |
| 5,532,274 | A | 7/1996 | Wenzel et al. |
| 5,607,969 | A * | 3/1997 | Milman et al. ............... 514/538 |
| 5,881,926 | A | 3/1999 | Ross |
| 6,166,081 | A | 12/2000 | Kushnir |
| 6,531,153 | B2 | 3/2003 | Seth |
| 6,703,424 | B2 | 3/2004 | Levin et al. |
| 2001/0053373 | A1 * | 12/2001 | D'Silva |
| 2004/0247628 | A1 * | 12/2004 | Lintz et al. |
| 2005/0070608 | A1 | 3/2005 | Remenar et al. |

FOREIGN PATENT DOCUMENTS

| | | | |
|---|---|---|---|
| CA | 2143070 | | 8/1995 |
| EP | 0 287 341 A1 | | 10/1988 |
| IE | 0062643 | | 2/1995 |
| JP | 79014167 B | * | 12/1970 |
| JP | 54-105221 | | 8/1979 |
| JP | 2006-524820 A | | 11/2006 |
| SE | 512655 | | 4/2000 |
| WO | WO 98/16208 | | 4/1998 |
| WO | WO 03/041646 | | 5/2003 |
| WO | WO 03/053400 | | 7/2003 |
| WO | WO 2005/023185 | | 3/2005 |
| WO | WO 2006/006929 | | 1/2006 |

OTHER PUBLICATIONS

Munson et al, Principles of Pharmacology—Basic Concepts & Clinical Applications, 1995, Chapman & Hall, pp. 328-333.*
Remington's Pharmaceutical Sciences, 1975, Mack Publishing Co., 15th Edition, pp. 200-203.*
South et al., "Iron binding by tannic acid: effects of selected ligands", 1998. Food Chemistry, vol. 63(2), pp. 167-172.*
Pappert et al., Movement Disorders, 1997, vol. 12(4), pp. 608-610.*
Dawson et al., Neurotoxicity Research, 2000, vol. 2, pp. 1-15.*
Connors et al., Chemical Stability of Pharmaceuticals: A Handbook for Pharmacists, 2nd Edition,1986, pp. 93, 94, 99, and 100.*
Parikh, D. H., Handbook of Pharmaceutical Granulation Technology, 1997, Marcel Dekker, Inc., pp. 1-2.*
The Merck Index, 12th Edition, 1996, "Sodium Benzoate", p. 8726.*
U.S. Environmental Protection Agency, "Secondary Drinking Water Regulations: Guidance for Nuisance Chemicals", 1992, EPA 810/K-92-001, downloaded on Aug. 2, 2010 from "http://www.epa.gov/ogwdw000/consumer/2ndstandards.html", pp. 1-5 of 5.*
Stennett, D., "Stability of levodopa in 5% dextrose injection at pH 5 or 6", American Journal of Hospital Pharmacy, vol. 43, pp. 1726-1728 (1986).
Weintraub et al., "IV levodopa preparation and sterilization by filtration", Hospital formulary, vol. 20, pp. 226, 930 (1985).
Slates et al., J. Org. Chem., 29 (1964), pp. 1424-1429.
Titus et al., Journal of Chromatography, 534 (1990), pp. 87-100.
Tömpe et al., Analytica Chimica Acta, 273 (1993), pp. 391-398.
Vickers, et al., Drug Metabolism and Disposition, vol. 2, No. 1 (1974), pp. 9-22.
Vickers et al., Journal of Medicinal Chemistry, vol. 18, No. 2, (1975), pp. 134-138.
Levomet® ATC: N04BA01, levodopa methyl chloride (product label in Italian, with English translation provided), 2002.
Allen, L., Editor, International Journal of Pharmaceutical Compounding, vol. 6, No. 3, (May/Jun. 2002), p. 202.
ATSDR, "Toxicological Profile for Hydrazines", Public Health Service, U.S. Dept of Health and Human Services, 1997, http://www.atsdr.cdc.gov/toxprofiles/phs100.html.
Au et al., Biochem, J., 129 (1972) pp. 1-10.
Bertoldi et al., Biochemistry, 37 (1998), pp. 6552-6561.
Carlin et al., Journal of Pharmaceutical and Biomedical Analysis, 17 (1998), pp. 885-890.
Kurth, M., Drugs & Aging, 10 (1997), pp. 332-340.
Kurth et al., Neurology, 43 (1993), pp. 1036-1039.
Metman et al., Movement Disorders, vol. 9, No. 4 (1994), pp. 463-465.
Pappert et al., Movement Disorders, vol. 11, No. 1 (1996), pp. 24-26.
Parkinson's Syndrome, How to Make and Take Liquid Sinemet, http://james.parkinsons.org.uk/Brian/SinemetL.pdf, (2003).
Japanese Pharmaceutical Excipients Directory (1994), p. 18, published by Yakuji Nippo Limited, Tokyo, Japan (with translation of relevant portions of a Japanese Office Action in which the reference was cited and translation of relevant portions of the reference).

* cited by examiner

*Primary Examiner* — Savitha Rao
*Assistant Examiner* — Gregg Polansky
(74) *Attorney, Agent, or Firm* — RatnerPrestia

(57) ABSTRACT

The present invention relates to stable dosage forms and compositions of levodopa and carbidopa for the treatment of patients suffering from Parkinson's disease. The dosage forms and compositions comprise both solid and liquid formulations and result in stable pharmaceutical products. Such dosage forms and compositions comprise a metal chelator and a levodopa concentration from about 1 mg/mL to about 30 mg/mL.

23 Claims, 1 Drawing Sheet

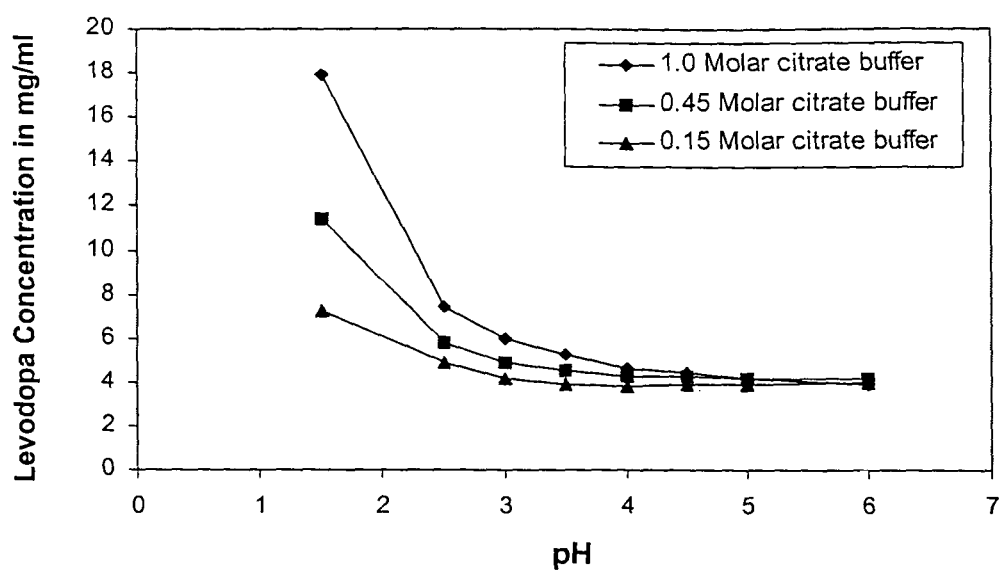

PHARMACEUTICAL COMPOSITIONS AND METHOD OF USING LEVODOPA AND CARBIDOPA

RELATED APPLICATIONS

This application is a continuation in part of U.S. patent application Ser. No. 10/926,702 filed Aug. 26, 2004 and PCT/US04/27607 filed Aug. 26, 2004 and claims priority to U.S. Application No. 60/499,256 filed on Aug. 29, 2003; U.S. Provisional Application No. 60/505,551 filed on Sep. 24, 2003, U.S. Provisional Application No. 60/559,864 filed on Apr. 6, 2004, and U.S. Provisional Application No. 60/586,442 filed on Jul. 8, 2004.

FIELD OF THE INVENTION

This invention relates to stable compositions of levodopa and carbidopa.

BACKGROUND OF THE INVENTION

Parkinson's disease is a neurodegenerative disorder characterized by a progressive degeneration of the dopaminergic pathway in the brain. Parkinson's patients often have symptoms of bradykinesia, rigidity, tremor, poor balance and difficulty walking. Simple movements such as making breakfast or coffee can be very difficult for Parkinson's disease patients. In particular, manipulating small items such as a pill can be very difficult. One of the most common treatments for Parkinson's disease is administration of levodopa. Levodopa functions to cross the blood brain barrier, convert to dopamine, and to replace or supplement low levels of dopamine in the brain. Parkinson's disease patients often take between 200 mg and 2 g of levodopa per day with late stage Parkinsons patients taking toward the later end of this range. Monotherapy with levodopa is often accompanied by unpleasant side effects such as nausea and vomiting. Administration of a combination of levodopa and a dopa decarboxylase inhibitor such as carbidopa decreases the patient side effects while increasing drug efficacy. One of the disadvantages with levodopa/carbidopa tablets is that Parkinson's patients often experience episodes of "wearing off" During these episodes, patients become frozen or have rigid movements. These freezing episodes have significant detrimental consequences to the quality of life for Parkinson's patients. To recover from a freezing episode, patients often administer levodopa/carbidopa tablets under their tongue. Administration of the drug under a patient's tongue will often not release a patient from a frozen episode for an hour. A controlled release version of levodopa/carbidopa tablets (SINEMET CR) is also available to patients. The controlled release version of SINEMET has not provided much better clinical affects. Thus, patients taking SINEMET CR still have "wearing off" and frozen episodes. One of the methods patients have used to avoid or fix these "wearing off" episodes is to create a liquid version of levodopa/carbidopa. Stable liquid levodopa/carbidopa formulations do not exist. Unstable liquid levodopa/carbidopa suspension is a home remedy Parkinson's patients have employed. Patients take a sip of the unstable liquid levodopa/carbidopa suspension when they feel their levodopa levels decreasing. Thus, patients self dose their levodopa concentrations and subsequently their Parkinson's symptoms. Methods of making unstable liquid levodopa/carbidopa are available in the literature. Typically, patients grind up a pill of levodopa/carbidopa and add a liquid such as orange juice or ginger ale. One of the disadvantages of this procedure is the grinding process. A patient entering a "wearing off" episode can have significant difficulty in grinding a pill. The strength and finger manipulation necessary to grind a pill can be missing or inadequate during a wearing off episode. In addition, this unapproved mixing can result in incomplete bioavailability of the levodopa or carbidopa or poor stability. Carbidopa and levodopa are unstable compounds in liquid for long periods of time, and currently there are no stable carbidopa and levodopa liquid formulations. Thus, a need exists for a liquid formulations of carbidopa and levodopa which are safer, more stable, and easier to use than current suspensions.

SUMMARY OF THE INVENTION

Surprisingly, it has now been found that new stable formulations of carbidopa and levodopa can be obtained which can readily be combined with a liquid and used to treat Parkinson's disease patients.

In one aspect, the present invention provides for a dry, solid, tablet, or powder formulation of carbidopa and levodopa which can be mixed with a liquid to form a stable pharmaceutical product.

In another aspect, the present invention provides for a method of treating a Parkinson's disease patient with a liquid formulation of carbidopa and levodopa.

In a further embodiment, a pharmaceutical composition comprises levodopa, carbidopa, acid and a metal chelator. Examples of metal chelators include EDTA and deferoxamine mesylate. The EDTA may be in the form of a salt or its free base. In one aspect, EDTA concentration is at least 0.01 mg/ml.

In another embodiment the acid can be selected from a carboxylic acid, a mineral acid, citric acid, tartaric acid, ascorbic acid, dehydroascorbic acid, acetic acid, formic acid, methanoic acid, butanoic acid, ethanoic acid, benzoic acid, butyric acid, malic acid, propionic, epoxysuccinic acid, muconic acid, furanacrylic acid, citramalic acid, capric acid, stearic acid, caproic acid, malonic acid, succinic acid, diethylacetic acid, methylbutyric acid, hydrochloric acid, hydrobromic acid, phosphoric acid, nitric acid, or sulfuric acid.

In one embodiment, the composition is a stable liquid of levodopa and carbidopa. In one aspect, the stable liquid has less than 10% of carbidopa degradation at 25° C. after 7 days. In another aspect, the stable liquid has less than 5% of carbidopa degradation at 25° C. after 7 days. In further aspect, the stable liquid has less than 10% of carbidopa degradation at 25° C. after 30 days. In an additional aspect, the stable liquid has less than 5% of carbidopa degradation at 25° C. after 4 days. In another aspect, the stable liquid has less than 5% of carbidopa degradation at 4° C. after 30 days. In one aspect, the stable liquid has less than 5% of carbidopa degradation at 25° C. after 250 days. In a further aspect, the stable liquid has less than 5% of carbidopa degradation at 4° C. after 360 days. In an additional aspect, the stable liquid has less than 10% of carbidopa degradation at 25° C. after 9 days.

In an additional embodiment, a pharmaceutical composition comprises levodopa, carbidopa and acid wherein the pH of said composition is less than or about 3.0. In one aspect, this composition has less than 10% of carbidopa degradation at 25° C. after 7 days. In another aspect, this composition has less than 5% of carbidopa degradation at 25° C. after 7 days. In further aspect, this composition has less than 10% of carbidopa degradation at 25° C. after 30 days. In an additional aspect, this composition has less than 5% of carbidopa degradation at 25° C. after 4 days. In another aspect, this composition has less than 5% of carbidopa degradation at 4° C. after 30 days. In one aspect, this composition has less than 5% of carbidopa degradation at 25° C. after 250 days. In a further aspect, this composition has less than 5% of carbidopa degradation at 4° C. after 360 days. In an additional aspect, this composition has less than 10% of carbidopa degradation at 25° C. after 9 days. In a further aspect, this composition further comprises further an artificial sweetener or a preservative.

In another embodiment, an aqueous composition comprises levodopa and carbidopa wherein the levodopa is at a concentration of between 2.5 mg/ml and 9 mg/ml. In another embodiment, the levodopa is at a concentration of about 4 mg/ml. In one aspect, this composition has less than 10% of carbidopa degradation at 25° C. after 7 days. In another aspect, this composition has less than 5% of carbidopa degradation at 25° C. after 7 days. In further aspect, this composition has less than 10% of carbidopa degradation at 25° C. after 30 days. In an additional aspect, this composition has less than 5% of carbidopa degradation at 25° C. after 4 days. In another aspect, this composition has less than 5% of carbidopa degradation at 4° C. after 30 days. In one aspect, this composition has less than 5% of carbidopa degradation at 25° C. after 250 days. In a further aspect, this composition has less than 5% of carbidopa degradation at 4° C. after 360 days. In an additional aspect, this composition has less than 10% of carbidopa degradation at 25° C. after 9 days. In a further aspect, this composition further comprises further an artificial sweetener or a preservative.

In a further embodiment, a composition comprises levodopa, carbidopa, acid, and a metal chelator wherein less than 1.2% of the carbidopa has degraded after 24 hours at 25° C. Examples of metal chelators include EDTA and deferoxamine mesylate.

Another embodiment comprises compositions of levodopa, carbidopa, acid, and a metal chelator wherein less than 2.4% of the carbidopa has degraded after 48 hours at 25° C.

Additional compositions of this invention comprise stable formulations with low levels of degradants. In one aspect, a degradant of hydrazine is lower than currently available levodopa/carbidopa suspensions. In one aspect, a liquid pharmaceutical composition comprises levodopa and carbidopa at about 0.4 to 1.5 mg/ml, wherein hydrazine levels are below 0.07 ug/ml after 24 hours at 25° C. In another aspect, a liquid pharmaceutical composition comprises levodopa and carbidopa at about 0.4 to 1.5 mg/ml, wherein hydrazine levels are below 0.32 ug/ml after 3 days at 25° C. In a further aspect, a liquid pharmaceutical composition comprises levodopa and carbidopa at about 0.4 to 1.5 mg/ml, wherein hydrazine levels are below 1.6 ug/ml after 7 days at 25° C. In a still further aspect, a liquid pharmaceutical composition comprises levodopa and carbidopa at about 0.4 to 1.5 mg/ml, wherein hydrazine levels are below 0.06 ug/ml after 7 days at 4° C.

In one embodiment, a liquid formulation of levodopa, carbidopa, acid and a metal chelator is clear or translucent.

In an additional embodiment, a pharmaceutical composition comprises levodopa, carbidopa, acid and a thioether compound. In one aspect, the thioether functions to stabilize the carbidopa. Examples of thioethers include methionine, cysteine, glutathione, thioglycerol, sodium thiosulfate, and n-acetylmethionine. In another embodiment, a composition comprises levodopa, carbidopa, acid, a thioether and a metal chelator. One embodiment contains a pharmaceutical composition comprising levodopa at about 2.5 to 6 mg/ml, carbidopa at about 0.625 to 1.5 mg/ml, citric acid at about 5 mg/ml to 10 mg/ml, and EDTA at greater than about 0.25 mg/ml. This composition may additionally contain aspartame at about 0.1 mg/ml to about 1 mg/ml or sodium benzoate at about 0.01 mg/ml to about 1 mg/ml.

In a further embodiment, a pharmaceutical composition comprises levodopa at about 2.5 to 6 mg/ml, carbidopa at about 0.25 to 0.6 mg/ml, citric acid at about 5 mg/ml to 10 mg/ml, and EDTA at greater than about 0.25 mg/ml. This composition may additionally contain water, aspartame at about 0.1 mg/ml to about 1 mg/ml, or sodium benzoate at about 0.01 mg/ml to about 1 mg/ml.

In one embodiment, a pharmaceutical composition comprises levodopa of about 500 mg to about 1500 mg, carbidopa of about 125 mg to about 375 mg, citric acid of about 1065 mg to about 3195 mg and EDTA of about 13 mg to about 41 mg. This composition may be in the form of a dispersible tablet or in the form of a powder or granules for mixing with a liquid.

In another embodiment, a pharmaceutical composition comprises levodopa of about 1000 mg, carbidopa of about 250 mg, citric acid of about 2130 mg, and EDTA of about 27 mg. The composition can further comprise water, aspartame or sodium benzoate.

One embodiment comprises a pharmaceutical composition of levodopa, carbidopa, acid, a metal chelator, and sugar wherein the sugar comprises less than 1% of the composition.

One embodiment comprises a method of dosing levodopa and carbidopa wherein a dry or solid formulation of levodopa and carbidopa is added to a liquid; the formulation is mixed for less than 10 minutes and the formulation is adminstered to a patient. In one aspect of this invention, the administration of the formulation is the first morning dose for a Parkinson's disease patient.

In another embodiment, a liquid composition is capable of dissolving levodopa at about 2.5 to 6 mg/ml and carbidopa at about 0.25 to 0.6 mg/ml. In one aspect, this composition has less than 10% of carbidopa degradation at 25° C. after 7 days. In another aspect, this composition has less than 5% of carbidopa degradation at 25° C. after 7 days. In further aspect, this composition has less than 10% of carbidopa degradation at 25° C. after 30 days. In an additional aspect, this composition has less than 5% of carbidopa degradation at 25° C. after 4 days. In another aspect, this composition has less than 5% of carbidopa degradation at 4° C. after 30 days. In one aspect, this composition has less than 5% of carbidopa degradation at 25° C. after 250 days. In a further aspect, this composition has less than 5% of carbidopa degradation at 4° C. after 360 days. In an additional aspect, this composition has less than 10% of carbidopa degradation at 25° C. after 9 days.

A further embodiment of this invention is a method of making a pharmaceutical composition to treat a dopamine disorder comprising the steps of combining levodopa, carbidopa, acid, a metal chelator; and water.

In one embodiment, a liquid composition comprises levodopa and carbidopa wherein the total metal ion concentration is less than 1 ppm. In another aspect, the free metal ion concentration is less than 1 ppm. In one aspect, the composition further comprises an acid. One example of a relevant acid is hydrochloric acid. In other compositions the total metal ion concentration may be below 0.1 ppm, 0.1 ppm, 0.01 ppm, or 1 ppb.

In one method of this invention, a formulation of levodopa and carbidopa comprises one or more excipients or active agents and these excipients or active agents are subjected to chromatography to remove metal ions. Examples of applicable metal ions to remove include iron, lead, zinc or aluminum.

Additional aspects of this invention comprise administering a composition of this invention to a patient.

BRIEF DESCRIPTION OF THE DRAWINGS

FIG. 1: Demonstrates the solubility of levodopa in citrate buffer as a function of pH and levodopa concentration.

DETAILED DESCRIPTION OF THE INVENTION

The present invention provides for stable pharmaceutical compositions comprising carbidopa and levodopa. Prior compositions of levodopa and carbidopa are not sufficiently stable or functional for Parkinson's disease patients. Compositions of this invention can provide advantages over currently marketed levodopa and carbidopa formulations and the current homemade versions of liquid levodopa/carbidopa.

"Liquid levodopa/carbidopa" is defined to be a formulation of levodopa, carbidopa and a liquid wherein one or more tablets of levodopa/carbidopa are combined with a liquid.

"Parkinson's disease patient" is defined to be any person diagnosed by a physician to be suffering from Parkinson's Disease or any person diagnosed to be suffering from a dopamine disorder who could benefit from levodopa treatment.

Improvements in stabilizing compositions of levodopa and carbidopa have been found. One method of improving stability involves reducing the free metal concentration in compositions of levodopa and carbidopa. Another method of improving stability involves reducing the pH of a liquid composition of levodopa and carbidopa. A further method of improving stability involves selecting preferred acids for the stability of levodopa and carbidopa. Additional methods of improving stability of levodopa and carbidopa formulations include avoiding light exposure, addition of sulfides to the composition, and elimination or reduction in aldehydes and ketones in the composition (such as sugars).

This invention provides for formulations of carbidopa and levodopa which have advantages over the prior art in stability and ease of use. It has been found that the currently used homemade versions of liquid levodopa/carbidopa produce multiple degradation products. At least one of these degradation products is hydrazine, a potential carcinogen. Current practice by late stage Parkinson's patients who take 1 g of levodopa per day in the form of liquid levodopa/carbidopa could be exposed to toxic levels of hydrazine. Even though current liquid levodopa/carbidopa formulations provide significant benefit to late stage Parkinson's patients, these homemade formulations expose patients to a potential carcinogen. This potential carcinogen has been linked with cancer. ("Toxicological Profile for Hydrazines," US Department of Health and Human Services, September 1997). In addition, the degradation of carbidopa to hydrazine results in lost carbidopa potency, thereby decreasing the shelf life of a product.

A need exists for formulations which are stable and easy for Parkinson's patients to use while still providing the benefit of a liquid formulation of levodopa and carbidopa. A significant effort was made to create liquid formulations comprising levodopa and carbidopa which are stable. After significant testing, it was found that metals destabilize carbidopa. One embodiment of this invention contains levodopa, carbidopa, and a metal chelator. Without being bound to any theory, metal ions are believed to cause carbidopa degradation (Example 12). Examples of chelators include, but are not limited to, EDTA, deferoxamine mesylate, EGTA, fumaric acid, and malic acid. Included within the definition of EDTA are both free acid and salt forms of EDTA. Examples of free acid or salt forms of EDTA include editic acid, disodium edetate, dipotassium edetate, edetate calcium disodium, sodium edetate, and trisodium edetate. Any of editic acid, disodium edetate, dipotassium edetate, edetate calcium disodium, sodium edetate, and trisodium edetate may be excluded from some embodiments of this invention. In one embodiment, EDTA concentration is at least 0.01 mg/ml, at least 0.05 mg/ml, at least 0.1 mg/ml, between 0.01 and 0.5 mg/ml, between 0.05 mg/ml and 0.3 mg/ml, between 0.05 mg/ml and 0.2 mg/ml or about 0.1 mg/ml. In one embodiment, the metal chelator is a salt.

In a further embodiment, compositions of this invention contain low levels of metal, no detectable metal, low levels of free metal ions, or no detectable free metal ions. In one embodiment, low levels of metal are less than 10 ppm of metal ion, 8 ppm of metal ion, 5 ppm of metal ion, 3 ppm of metal ion, 2 ppm of metal ion, 1 ppm of metal ion, less than 0.9 ppm of metal ion, less than 0.8 ppm of metal ion, less than 0.7 ppm of metal ion, less than 0.6 ppm of metal ion, less than 0.5 ppm of metal ion, less than 0.4 ppm of metal ion, less than 0.3 ppm of metal ion, less than 0.2 ppm of metal ion, less than 0.1 ppm of metal ion, less than 0.08 ppm of metal ion, less than 0.05 ppm of metal ion, less than 0.02 ppm of metal ion, less than 0.01 ppm of metal ion, less than 8 ppb of metal ion, less than 5 ppb of metal ion, less than 3 ppb of metal ion or less than 1 ppb of metal ion. In another embodiment, low levels of free metal are less than 10 ppm of free metal ion, 8 ppm of free metal ion, 5 ppm of free metal ion, 3 ppm of free metal ion, 2 ppm of free metal ion, 1 ppm of free metal ion, less than 0.9 ppm of free metal ion, less than 0.8 ppm of free metal ion, less than 0.7 ppm of free metal ion, less than 0.6 ppm of free metal ion, less than 0.5 ppm of free metal ion, less than 0.4 ppm of free metal ion, less than 0.3 ppm of free metal ion, less than 0.2 ppm of free metal ion, less than 0.1 ppm of free metal ion, less than 0.08 ppm of free metal ion, less than 0.05 ppm of free metal ion, less than 0.02 ppm of free metal ion, less than 0.01 ppm of free metal ion, less than 8 ppb of free metal ion, less than 5 ppb of free metal ion, less than 3 ppb of free metal ion or less than 1 ppb of free metal ion. In a further embodiment, compositions with low levels of metal ions contain from 1 ppm of metal ions to 1 ppb metal ions, from 1 ppm of metal ions to 10 ppb metal ions, from 1 ppm of metal ions to 0.01 ppm metal ions, from 0.5 ppm of metal ions to 1 ppb metal ions, from 0.5 ppm of metal ions to 0.01 ppm metal ions, from 0.5 ppm of metal ions to 10 ppb metal ions, from 2 ppm of metal ions to 1 ppb metal ions, or from 0.8 ppm of metal ions to 1 ppb metal ions. In a still further embodiment, compositions with low levels of free metal ions contain from 1 ppm of free metal ions to 1 ppb free metal ions, from 1 ppm of free metal ions to 10 ppb free metal ions, from 1 ppm of free metal ions to 0.01 ppm free metal ions, from 0.5 ppm of free metal ions to 1 ppb free metal ions, from 0.5 ppm of free metal ions to 0.01 ppm free metal ions, from 0.5 ppm of free metal ions to 10 ppb free metal ions, from 2 ppm of free metal ions to 1 ppb free metal ions, or from 0.8 ppm of free metal ions to 1 ppb free metal ions. Different embodiments of this invention can function to limit free metal ions in both solid and liquid compositions. In other embodiments, compositions may have low levels of specific metal ions. The ranges listed for metal ions are intended to be applicable to specific metal ions also. For example, a composition may have less than 1 ppm of iron. As another example, a composition of this invention may have between 1 ppm and 1 ppb of iron. Examples of metal ions include, but are not limited to, iron, calcium, magnesium, cobalt, copper, iron, manganese, molybdenum, selenium, zinc, aluminum, arsenic, barium, cadmium, chromium, lead, mercury, selenium and silver. In one specific embodiment, a composition of levodopa and carbidopa contains less than 1 ppm of a metal ion. In a further embodiment, a composition of levodopa, carbidopa and acid contains less than 1 ppm of a metal ion. In a still further embodiment, a composition of levodopa and carbidopa contains less than 0.1 ppm of a metal ion. In another embodiment, a composition of levodopa, carbidopa and acid contains less than 0.1 ppm of a metal ion. In some embodiments, the total metal concentration is below a specific level and in other embodiments the total free metal ion concentration is below a specific level. Free metal ions are metal ions which are not bound chemically to other molecules, excluding water.

Metal ions occur in trace amounts in many pharmaceutical preparations including in commercially available preparations of levodopa and carbidopa. In addition, metal ions are present in liquids which could be used in making liquid formulations of levodopa and carbidopa. Methods of this invention remove metal ions from active ingredients, excipients, such as binders, acids, flavors, and from diluents such as water. In one embodiment, compositions of this invention are made by removing metal ions by chromatography. In an additional embodiment, compositions of this invention are made by subjecting all or some excipients and active agents to chromatography. In a further embodiment, compositions of this invention are made by subjecting all or some excipients and active agents to chromatography such that the total metal ion concentration of the resulting composition is less than 1 ppm, less than 0.5 ppm, less than 0.1 ppm, less than 0.01 ppm, or less than 1 ppb. In another embodiment, a composition of levodopa and carbidopa is subjected to chromatography to remove metal ions. Metal ions can be removed from a final composition or from each individual excipient or active from a composition. For example, metal ions could be removed from a formulation of levodopa, carbidopa, and hydrochloric acid or metal ions could be removed from levodopa, carbidopa, and hydrochloric acid individually. In another embodiment, levodopa and carbidopa are mixed with deionized water.

In addition, thioether compounds have been found to stabilize the carbidopa molecule thereby decreasing the degradant formation. Examples of thioethers include, but are not limited to, methionine, cysteine, glutathione, thioglycerol, sodium thiosulfate, and n-acetylmethionine.

Additional embodiments of this invention contain both a thioether and a chelator. The combination of a thioether and a chelator functions to significantly lower the level of carbidopa degradation in compositions of carbidopa and levodopa. Thus, in one embodiment, this invention includes carbidopa, levodopa and one or more agents selected from a metal chelator or a thioether. A further aspect of this invention is a formulation of carbidopa, levodopa and one or more agents selected from a chelator or a thioether wherein less than 10% of carbidopa degrades after 7 days at 25° C.

In one embodiment, compositions of this invention are stable. Stable compositions have less than 10% carbidopa degradation at 25° C. after 7 days, less than 5% carbidopa degradation at 25° C. after 7 days, less than 10% carbidopa degradation at 25° C. after 30 days, less than 5% carbidopa degradation at 25° C. after 4 days, less than 5% carbidopa degradation at 4° C. after 30 days, less than 5% carbidopa degradation at 25° C. after 250 days, less than 5% carbidopa degradation at 4° C. after 360 days, or less than 10% carbidopa degradation at 25° C. after 9 days. Embodiments of this invention enable formulations with degradant levels below 1 part per million (ppm), below 0.5 ppm, below 0.2 ppm, below 0.1 ppm, below 0.05 ppm, or below 0.01 ppm after storage for 24 hours at room temperature. Embodiments of this invention enable formulations with one specific degradant such as hydrazine with levels below 1 part per million (ppm), below 0.5 ppm, below 0.2 ppm, below 0.1 ppm, below 0.05 ppm, or below 0.01 ppm after storage for 48 hours at room temperature. Embodiments of this invention enable formulations with hydrazine levels below 1 part per million (ppm), below 0.5 ppm, below 0.2 ppm, below 0.1 ppm, below 0.05 ppm, or below 0.01 ppm after storage for one week at 4 degrees Celcius.

In one embodiment, liquid formulations of this invention have less than 15%, 10%, 5%, 3%, 2%, 1%, 0.5%, or 0.25% degradation of carbidopa after one day at 25° C. In another embodiment, liquid formulations of this invention have less than 15%, 10%, 5%, 3%, 2%, 1%, 0.5%, or 0.25% degradation of carbidopa after three days at 25° C. In one embodiment, liquid formulations of this invention have less than 15%, 10%, 5%, 3%, 2%, 1%, 0.5%, or 0.25% degradation of carbidopa after one week at 25° C. In one embodiment, liquid formulations of this invention have less than 15%, 10%, 5%, 3%, 2%, 1%, 0.5%, or 0.25% degradation of carbidopa after one month at 25° C. In a further embodiment, carbidopa monohydrate is used to aid in carbidopa stability.

In another embodiment, the compositions of the present invention comprising levodopa are suitably stable for pharmaceutical use. In one embodiment, the levodopa, carbidopa or formulations thereof in the form of a liquid of the present invention are stable such that when stored at room temperature for 24 hours, less than 1% of any one degradant is formed. The term degradant refers herein to product(s) of a single type of chemical reaction. For example, if a hydrolysis event occurs that cleaves a molecule into two products, for the purpose of the present invention, it would be considered a single degradant. In other embodiments, when stored at 4 degrees C. for one week, compositions contain less than 5% of any one degradant is formed. Alternatively, when stored at room temperature for 24 hours, compositions of this invention contain less than 10%, less than 5%, less than 3%, less than 2%, less than 1%, less than 0.5% of any one degradant. The relative humidity (RH) may be specified as ambient RH, 75% RH, or as any single integer between 1 to 99% RH. One specific type of degradant is hydrazine.

In an additional embodiment, compositions of this invention have improved stability over current practice. In one example, compositions of this invention have 100 times less carbidopa degradation than current practice of mixing ginger ale with SINEMET tablets (at 1 mg/ml) after storage at 25° C. for 24 hours. In another example, compositions of this invention have 3 times less carbidopa degradation than current practice of mixing orange juice with SINEMET tablets (at 1 mg/ml) after storage at 25° C. for 24 hours. In another example, compositions of this invention have 15 times less carbidopa degradation than current practice of mixing orange juice with SINEMET tablets (at 1 mg/ml) after storage at 25° C. for 3 days. In an additional example, compositions of this invention have 60 times less carbidopa degradation than current practice of mixing orange juice with SINEMET tablets (at 1 mg/ml) after storage at 25° C. for 7 days.

In some embodiments of this invention, the compositions have lower levels of carbidopa degradation compared to current practice. It has been found that the currently used liquid levodopa/carbidopa has carbidopa degradants in the homemade formulation (see Example 3 and 6). For example, patients are often encouraged to mix levodopa/carbidopa tablet with orange juice, which contains ascorbic acid to dissolve the levodopa/carbidopa tablet. The ascorbic acid can cause a reaction which creates a carbidopa degradant. These degradants may cause negative biological affects and decreased drug potency because degraded drug in no longer functional. Experiments with other acids have demonstrated that other carbidopa degradants are possible. Two specific degradants which can form in liquid levodopa/carbidopa formulations are hydrazine and 3,4-dihydroxyphenylacetone (DHPA). Without being bound to any particular theory, it is believed that carbidopa degrades to DHPA and hydrazine in equal proportions. Thus, the presence of DHPA can indicate the presence of hydrazine. Compositions of this invention decrease the levels of these degradants. For example, compositions of this invention may prevent formation of these degradants or keep formation of these degradants below 0.05%, below 0.1%, below 0.2%, below 0.3%, below 0.5%, below 1%, below 2%, below 5%, or below 10% after storage at 25° C. for one week.

In another embodiment, the compositions of the present invention comprising levodopa are suitably stable for pharmaceutical use. Preferably, the levodopa, carbidopa or formulations in a solid dosage form thereof the present invention are stable such that when stored at 30 degrees C. for 2 years, less than 0.2% of any one degradant is formed. The term degradant refers herein to product(s) of a single type of chemical reaction. For example, if a hydrolysis event occurs that cleaves a molecule into two products, for the purpose of the present invention, it would be considered a single degradant. More preferably, when stored at 40 degrees C. for 2 years, less than 0.2% of any one degradant is formed. Alternatively, when stored at 30 degrees C. for 3 months, less than 0.2% or 0.15%, or 0.1% of any one degradant is formed, or when stored at 40 degrees C. for 3 months, less than 0.2% or 0.15%, or 0.1% of any one degradant is formed. Further alternatively, when stored at 60 degrees C. for 4 weeks, less than 0.2% or 0.15%, or 0.1% of any one degradant is formed. The relative humidity (RH) may be specified as ambient RH, 75% RH, or as any single integer between 1 to 99% RH.

One embodiment of this invention comprises compositions of carbidopa, levodopa and one or more acids. Examples of acids include, but are not limited, to carboxylic acids, mineral acid salts, citric acid, tartaric acid, ascorbic acid, dehydroascorbic acid, acetic acid, formic acid, methanoic acid, butanoic acid, ethanoic acid, benzoic acid, butyric acid, malic acid, propionic, epoxysuccinic acid, muconic acid, furanacrylic acid, citramalic acid, capric acid, stearic acid, caproic acid, malonic acid, succinic acid, diethylacetic acid, methylbutyric acid, hydrochloric acid, hydrobromic acid, phosphoric acid, nitric acid, and sulfuric acid. Acid can be added at molar ratios of from about 0.5 moles of levodopa to about 20 moles of acid, from about 0.5 moles of levodopa to about 2 moles of acid, from about 1 mole of levodopa to about 5 moles of acid, from about 1 mole of levodopa to about 7 moles of acid, from about 1 mole of levodopa to about 10 moles of acid, from about 1 mole of levodopa to about 3 moles of acid, or from about 1 mole of levodopa to about 4 moles of acid. One skilled in the art can increase the acid concentration to increase the level of carbidopa or levodopa which can be dissolved in a liquid. Included within this invention is the use of increasing ionic strength to increase the solubility of carbidopa or levodopa. For example, adding HCl into a composition of levodopa, carbidopa and citric acid could further solubilize the levodopa or could allow the solubilization of higher level of levodopa.

In some solid, powder or granule compositions of this invention, water can increase carbidopa degradation. Use of anhydrous acid components can aid in carbidopa stability. In one embodiment, a solid, powder or granule composition comprises levodopa, carbidopa, and an anhydrous acid. In another embodiment, a solid, powder or granule composition comprises levodopa, carbidopa, and anhydrous citric acid.

In some embodiments, any specific acid can be excluded from compositions of this invention. Examples of acids which can be specifically excluded include, but are not limited to, carboxylic acids, citric acid, tartaric acid, ascorbic acid, dehydroascorbic acid, acetic acid, formic acid, methanoic acid, butanoic acid, ethanoic acid, benzoic acid, butyric acid, malic acid, propionic, epoxysuccinic acid, muconic acid, furanacrylic acid, citramalic acid, capric acid, stearic acid, caproic acid, diethylacetic acid, methylbutyric acid, hydrochloric acid, malonic acid, succinic acid, phosphoric acid, and sulfuric acid.

Adjustments of ionic strength can be done to affect stability. Example 7 illustrates that salt can have a slightly negative effect on carbidopa stability. Thus, in some embodiments, ionic strength is adjusted to maintain optimal stability. For example, in some compositions salt concentration is less than 1 Molar, less than 0.75 Molar, less than 0.5 Molar, less than 0.3 Molar, less than 0.2 Molar, or less than 0.1 Molar.

The pH of a liquid levodopa/carbidopa formulation can affect the stability of the formulation. As demonstrated in Example 8, lowering pH can increase stability of the formulation. Compositions of this invention can have a pH between 1 and 10, between 1 and 8, between 2 and 8, between 2 and 6, between 2 and 4, between 2.5 and 4.5, between 2.5 and 4, between 2.5 and 3.5, between 3 and 8, between 3 and 6, between 3 and 5, between 3 and 4, between 1 and 4, between 1.5 and 3.5, between 2 and 3 or less than 5, less than 4, less than 3, less than 2.9, less than 2.8, less than 2.7, less than 2.6, less than 2.5, less than 2.4, less than 2.3, less than 2.2, less than 2.1, or less than 2.

In one embodiment, a composition of this invention comprises levodopa, carbidopa, and acid wherein the pH of said composition is between 1 and 3. In another embodiment, a composition of this invention comprises levodopa, carbidopa, and acid wherein the pH of said composition is between 1 and 2.8. In another embodiment, a composition of this invention comprises levodopa, carbidopa, and acid wherein the pH of said composition is between 1.8 and 2.8.

Pharmaceutical compositions of this invention may comprise levodopa, carbidopa, and one, two, three, four or more additional excipients or additives. Excipients or additives may be inert or may be active and may affect other composition components. Excipients or additives can include, but are not limited to, acids, bases, salts, surfactants, emulsifiers, detergents, binders, wetting agents, salts, polymers, solvents, antimicrobials, preservatives, fillers, sugars, alcohols, colorants, flavors, and buffers. Excipients can act to stabilize a formulation or to decrease or eliminate degradation of the active agents. Included as embodiments in this invention are compositions which contain any known excipients including those disclosed in the *Handbook of Pharmaceutical Additives* compiled by Michael and Irene Ash, Gower Publishing, 1995.

In some embodiments, any one or more specific agents can be excluded. Examples of agents which can be excluded include, but are not limited to, acids, bases, salts, surfactants, emulsifiers, detergents, binders, wetting agents, salts, polymers, solvents, antimicrobials, preservatives, fillers, sugars, alcohols, or additives disclosed in the *Handbook of Pharmaceutical Additives*.

Additional excipients may include a granulation binder. Specific granulation binders include, but are not limited to hydroxypropylcellulose and hydroxypropylmethylcellulose, and polyvinylpyrolidone. In one embodiment, a water soluble granulation binder is used in formulations of this invention. In another embodiment, between 3 and 10% by weight, 4 and 6% by weight, or 4 and 5% by weight binder is used.

In some embodiments, additional agents are added to the composition to prevent the formation of degradants. Any agent that suffices to limit, reduce, or inhibit the formation of degradants in compositions of this invention is envisioned. Specific examples include, but are not limited to, ammonium bisulfite, ammonium sulfite, ammonium thiosulfate, arsenic sulfide, arsenic trisulfide, calcium dithionite, chromous chloride, ferrous chloride, ferrous oxalate, β-mercaptoethanol, Dithiothreitol, Vitamin E, Vitamin C, beta-carotene, lycopene, and flavonoids.

One aspect of this invention provides for compositions of carbidopa and levodopa which can be used to treat a Parkinson's patient. In some Parkinson's disease patients, a liquid version of carbidopa and levodopa is more beneficial than other dosing forms. As Parkinson's disease progresses, patients often require continually higher doses of levodopa to maintain movement capabilities. These high level dosing requirements often leave patients more susceptible to freezing episodes. Thus, late stage Parkinson's patients often require high levels of levodopa to avoid freezing episodes. Some embodiments of this invention will be particularly useful to late stage Parkinson's patients to avoid freezing episodes or to quickly emerge from a freezing episode by providing high concentrations of levodopa to the patient quickly.

The present invention relates to formulations of levodopa and carbidopa can be produced as powders, tablets or granules and mixed with liquid to create a stable liquid formulation. These formulations can be used, for example, for administration to Parkinson's disease patients. The pharmaceutical compositions of this invention may take the form of several different embodiments. In one embodiment, levodopa and carbidopa are formulated as a dry packet which can be mixed with a liquid. In another embodiment, the levodopa and carbidopa are formulated as a pill or tablet which can be mixed with a liquid. In another embodiment, the levodopa and carbidopa can be formulated as any dosage form which can be mixed into a liquid. Examples of applicable dosage forms include, but are not limited to, powders, granules, tablets, capsules, dispersions, solutions, and gels.

Currently marketed levodopa and carbidopa drug products are in solid forms. Often Parkinson's patients may enter freezing episodes and have to wait extended periods for the pharmaceutical product to take its effect. This waiting and freezing period significantly inhibits the freedom and the safety of Parkinson's disease patients. Compositions of this invention may provide a faster onset of action thereby decreasing freezing time. In some embodiments, 80% or more of a composition of this invention may pass through the stomach and begin intestinal absorption within 1, 2, 3, 4, 5, 10, 15, 20, 25 or 30 minutes, or within 1 to 30, 1 to 20, 3 to 20, 3 to 15, 5 to 10, 10 to 30, 10 to 20, or 20 to 30 minutes, thereby speeding absorption into the body. In another embodiment, 90% or more of a composition of this invention may pass through the stomach and begin intestinal absorption within 1, 2, 3, 4, 5, 10, 15, 20, 25 or 30 minutes, or within 1 to 30, 1 to 20, 3 to 20, 3 to 15, 5 to 10, 10 to 30, 10 to 20, or 20 to 30 minutes, thereby speeding absorption into the body.

In addition, compositions of this invention may also include agents which increase stomach motility. One side effect of Parkinson's disease or Parkinson's disease drug therapy is decreased stomach motility. A formulation of levodopa, carbidopa, and a stomach motility modulator could provide Parkinson's disease patients with a fast acting drug. Examples of applicable drugs include, but are not limited to, dopamine antagonists such as cisapride and domperidone. One type of stomach modulator can function to relax the pyloric sphincter and to allow the stomach contents to enter the intestine. Drug formulations which increase stomach motility could allow dosage of levodopa and carbidopa with food. Many Parkinson's disease patients avoid eating food at a time close to their levodopa dosing schedule. Food is known to decrease levodopa absorption. A formulation of levodopa and carbidopa with a stomach motility agent could allow a patient to eat food while taking their necessary drug dose. Thus, one embodiment entails dosing a formulation of this inventions comprising levodopa, carbidopa and a stomach motility agent 1, 2, 3, 4, 5, 10, 20, 25, or 30 minutes before eating to decrease the effect food can have on levodopa bioavailability.

Embodiments of this invention with and without stomach motility agents may provide faster and more predictable levodopa absorption in the digestive system. Thus one aspect of this invention entails administering an embodiment of this invention with food or in close time proximity to a feeding period. Thus, levodopa absorption may not be affected by food in some embodiments of this invention. A further embodiment includes compositions which are administered with food or within on hour of eating.

In some embodiments, the bioavailability of the compositions of this invention may be higher than currently available marketed products. Higher bioavailability can result in a faster onset of action. For example, the compositions of this invention may increase the concentration of levodopa in the plasma to above 1 nMoles/ml, to above 2 nMoles/ml, to above 3 nMoles/ml, to above 4 nMoles/ml, to above 5 nMoles/ml to above 6 nMoles/ml, or to above 10 nMoles/ml. Compositions above 1 nMoles/ml, above 2 nMoles/ml, above 3 nMoles/ml, above 4 nMoles/ml, above 5 nMoles/ml, above 6 nMoles/ml, or above 10 nMoles/ml of levodopa may prevent, decrease or stop a freezing episode. Thus, in some embodiments of this invention, compositions can decrease or stop a freezing episode. In another embodiment, a composition of this invention can reach a level of 3 nMoles/ml of levodopa in plasma within 10 minutes of ingesting the composition, can reach a level of 3 nMoles/ml of levodopa in plasma within 15 minutes of ingesting the composition, can reach a level of 3 nMoles/ml of levodopa in plasma within 20 minutes of ingesting the composition, can reach a level of 4 nMoles/ml of levodopa in plasma within 10 minutes of ingesting the composition, can reach a level of 4 nMoles/ml of levodopa in plasma within 15 minutes of ingesting the composition, or can reach a level of 4 nMoles/ml of levodopa in plasma within 20 minutes of ingesting the composition. Patient reliance on levodopa varies. Thus, compositions of this invention can decrease, prevent, or stop a freezing episode by dosing to create an adequate levodopa plasma concentration. A doctor, pharmacist, or patient can adjust a dose of a formulation of this invention depending upon the particular circumstances of the Parkinson's disease patient.

Parkinson's patients often have difficulty swallowing a pill. Liquid formulations of levodopa and carbidopa can function to decrease or eliminate the difficulty of administering the medication. The current liquid levodopalcarbidopa homemade doses do not dissolve well in the liquid as described in the art. Thus, patients do not know if the carbidopa and levodopa are fully dissolved. In addition, currently described liquid levodopa/carbidopa formulations are typically administered at 1 mg/ml of levodopa and can require a Parkinson's patient to drink a liter or more of levodopa/carbidopa liquid per day. Large volumes of liquid can be difficult for a Parkinson's patient to swallow. The compositions of this invention can address these needs. Compositions of this invention can contain higher levels of levodopa or carbidopa than homemade liquid levodopa/carbidopa doses described in the art.

In some embodiments, the liquid formulation may contain a concentration of levodopa up to about 0.5 mg/ml, of up to about 1 mg/ml, of up to about 2 mg/ml, of up to about 3 mg/ml, of up to about 4 mg/ml, of up to about 5 mg/ml, of up to about 10 mg/ml, of up to about 20 mg/ml, of up to about 30 mg/ml or from about 0.5 mg/ml to 30 mg/ml, from about 0.5 mg/ml to 1 mg/ml, from about 1 mg/ml to 5 mg/ml, from about 1 mg/ml to 4 mg/ml, from about 1.5 mg/ml to 2 mg/ml, from about 1.5 mg/ml to 4 mg/ml, from about 2 mg/ml to 5 mg/m, from about 2 mg/ml to 7 mg/m, from about 3 mg/ml to 8 mg/ml, from about 5 mg/ml to 10 mg/ml, from about 4 mg/ml to 10 mg/ml, from about 4.5 mg/ml to 10 mg/ml, from about 4 mg/ml to 8 mg/ml, from about 4 mg/ml to 7 mg/ml, from about 4.5 mg/ml to 6 mg/ml, from about 4.5 mg/ml to 7 mg/ml, from about 4.5 mg/ml to 8 mg/ml, from about 7 mg/ml to 20 mg/ml, from about 10 mg/ml to 30 mg/m, from about 15 mg/ml to 20 mg/m, or from about 20 mg/ml to 30 mg/ml. In some embodiments, the liquid formulations of this invention may contain a concentration of carbidopa of up to 0.5 mg/ml, of up to about 1 mg/ml, of up to about 2 mg/ml, of up to about 3 mg/ml, of up to about 4 g/ml, of up to about 5 mg/ml, of up to about 10 mg/ml, of up to about 20, mg/ml, of up to about 30 mg/ml or from about 0.5 mg/ml to 30 mg/ml, from about 0.5 mg/ml to 1 mg/ml, from about 1 mg/ml to 5 mg/ml, from about 1 mg/ml to 4 mg/ml, from about 1.5 mg/ml to 2 mg/ml, from about 1.5 mg/ml to 4 mg/ml, from about 2 mg/ml to 5 mg/m, from about 2 mg/ml to 7 mg/m, from about 3 mg/ml to 8 mg/ml, from about 5 mg/ml to 10 mg/m, from about 7 mg/ml to 20 mg/ml, from about 10 mg/ml to 30 mg/ml, from about 15 mg/ml to 20 mg/m, or from about 20 mg/ml to 30 mg/ml.

The amount of levodopa or carbidopa to be dissolved can vary depending upon the needs of a patient. A skilled practitioner can determine the necessary dose. In addition, the ratio of carbidopa to levodopa can affect stability. Compositions of this invention can change the ratio of carbidopa to levodopa to decrease or eliminate degradants in the formulation and increase stability (see Example 5). The ratio of carbidopa to levodopa can function to stabilize carbidopa. Prior products contain ratios of 1:4 and 1:10 carbidopa:levodopa. Compositions of this invention can use other ratios which function to provide greater stability to the formulation. In some embodiments, the ratio of carbidopa to levodopa will be from one mole equivalent of carbidopa to three mole equivalents of levodopa, from one mole equivalent of carbidopa to four mole equivalents of levodopa, from one mole equivalent of carbidopa to five mole equivalents of levodopa, from one mole equivalent of carbidopa to six mole equivalents of levodopa, from one mole equivalent of carbidopa to seven mole equivalents of levodopa, from one mole equivalent of carbidopa to eight mole equivalents of levodopa, from one mole equivalent of carbidopa to nine mole equivalents of levodopa, from one mole equivalent of carbidopa to 10 mole equivalents of levodopa, from two mole equivalents of carbidopa to five mole equivalents of levodopa, from one mole equivalent of carbidopa to 15 mole equivalents of levodopa, from one mole equivalent of carbidopa to 20 mole equivalents of levodopa, from one mole equivalent of carbidopa to 25 mole equivalents of levodopa, or from two mole equivalents of carbidopa to nine mole equivalents of levodopa.

In one embodiment, compositions of this invention also comprise a thickening or gelling agent. Thickening or gelling agents can function to ease swallowing for Parkinson's disease patient. Examples of thickening or gelling agents include, but are not limited to, dextrin, ethyl cellulose, hydroxyethyl cellulose, hydroxyethylmethyl cellulose, hydroxypropyl cellulose, hypromellose, methylcellulose, polyethylene glycol, pectin, xantham gum, or zinc stearate.

The compositions of this invention allow easy swallowing of the formulation. Compositions may be mixed with aqueous or water based liquids. Examples of liquids include, but are not limited to, water, juice, tea, milk, carbonated beverages, saline, and dextrose solutions. Liquids which are commonly available in a home provide easy mixing and use. In addition, compositions of this invention may require minimal dosing volume. In one embodiment, liquids do not contain sugar or contain less than 1% sugar. Examples of sugar include fructose and sucrose. In some embodiments, patients can drink 100 mg of levodopa in a volume from about 5 ml to 500 ml, from about 5 ml to 100 ml, from about 10 ml to 75 ml, from about 15 ml to 50 ml, from about 20 ml to 30 ml, from about 10 ml to 25 ml, from about 25 to 50 ml, from about 50 ml to 250 ml, from about 25 ml to 100 ml, from about 50 ml to 100 ml, from about 75 ml to 200 ml, or from about 100 ml to 400 ml. In one embodiment, compositions are mixed with a liquid or water which has had its oxygen content depleted or reduced.

Compositions of this invention provide added stability beyond the stability of liquid levodopa/carbidopa. Examples 3 and 6 illustrate the stability problems associated with prior liquid levodopa/carbidopa formulations. Stable liquid formulations contain no phase separation, drug or excipient separation, and have minimal drug degradation. Compositions of the present invention can remain stable at 4 degrees Celsius for at least 2 hours, at least 4 hours, at least 6 hours, at least 12 hours, at least 24 hours, at least 36 hours, at least 2 days, at least 3 days, at least 4 days, at least 5 days, at least one week or at least one month. In addition, some compositions of this invention can be stable at room temperature (22 degrees Celsius) for at least 2 hours, at least 4 hours, at least 6 hours, at least 12 hours, at least 24 hours, at least 36 hours, at least 2 days, at least 3 days, at least 4 days, at least 5 days, at least one week, or at least one month.

One embodiment of the invention comprises a composition additionally containing a preservative, antibacterial, antimicrobial or bacteriostatic agent. Preservative, antibacterial, antimicrobial, and bacteriostatic agents can function to preserve the compositions both before mixing in liquid and after mixing in liquid. Examples of preservative, antibacterial, antimicrobial, or bacteriostatic agents include, but are not limited to, benzyl alcohol, metabisulfite, benzoic acid, butylparaben, chlorocresol, dimethylsulfoxide, ethylparaben, glacial acetic acid, imidurea, methylparaben, and propylparaben. One embodiment of this invention contains the preservative sodium benzoate. In one embodiment, compositions of this invention do not have any antibacterial or antimicrobial agent.

In some embodiments, additional agents can be added to improve the taste of the composition. Artificial sweeteners can be used to improve the taste of a composition. As shown in Example 9, sugars can decrease the stability of a liquid formulation of carbidopa and levodopa. Thus, in one embodiment compositions of this invention use less than 1% sugar. Some artificial sweeteners can be used to improve the taste of a formulation of this invention without causing the stability problems of sugars. Examples of artificial sweeteners includes aspartame, saccharin, sucralose, neotame and acesulfame potassium. One embodiment contains compositions with aspartame.

Included within this invention are compositions of levodopa and carbidopa in different physical forms. Examples of different physical forms of carbidopa and levodopa include, but are not limited to, pharmaceutically acceptable salts, solvates, co-crystals, polymorphs, hydrates, solvates of a salt, co-crystals of a salt, amorphous, and the free form of the drug. Depending upon the physical form of the carbidopa or levodopa, different sets of excipients may be needed in the formulation. Compositions of this invention may include a salt of levodopa or carbidopa to increase stability of the formulation. A salt such as HCl could function to lower the pH of the formulation and thereby increase stability of the formulation as shown in Example 11. Examples of inorganic acid addition salts for levodopa or carbidopa include hydrochloric, hydrobromic, sulfuric, sulfamic, phosphoric, and nitric acids. Examples of organic acid addition salts for levodopa or carbidopa include maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, and benzenesulfonic acids. In one embodiment, a composition comprises levodopa HCl, carbidopa and an acid. In another embodiment, a composition comprises levodopa, carbidopa HCl, and an acid.

Compositions of this invention may also contain a third, fourth, fifth active ingredient, or more. An additional active ingredient can function to augment or improve the treatment or conditions associated with Parkinson's disease. Examples of additional active ingredients include selegiline, COMT inhibitors such as entacapone or tolcapone, and dopamine agonists such as bromocriptine, ropinirole, pergolide, rotigotine, or pramipexole, dopamine decarboxylase inhibitors such as benserazide, and stomach motility modulators such as cisapride or domperidone.

Carbidopa functions as a peripheral dopamine decarboxylase inhibitor. Thus, carbidopa prevents or limits decarboxylation of levodopa in the peripheral system of the body, thereby allowing most levodopa to cross the blood brain barrier. Included within this invention are formulations substituting carbidopa with benserazide (another dopamine decarboxylase inhibitor).

In another embodiment of this invention, compositions can contain levodopa and/or carbidopa derivatives. Compositions can contain prodrugs such as levodopa and/or carbidopa ester derivatives. Examples of levodopa derivatives include, but are not limited to, levodopa esters including levodopa methyl ester, levodopa ethyl ester, and the like. Examples of carbidopa derivatives include, but are not limited to, esters including carbidopa methyl ester and carbidopa ethyl ester.

Another aspect of this invention provides for a composition of levodopa without any carbidopa. For some Parkinson's patients, plasma levels of carbidopa may be sufficient or patients may be taking other medications which contain carbidopa. Thus, carbidopa can be removed from any of the compositions of this invention. Patients can take a pill of carbidopa or benserazide and use a liquid formulation of levodopa. An additional embodiment comprises compositions of carbidopa without levodopa.

One embodiment of this invention comprises levodopa, carbidopa and a thioether. Specific examples of this thioether could include, but are not limited to, methionine or cysteine.

Another embodiment comprises levodopa, carbidopa and a metal chelator. Specific examples of metal chelators could include, but are not limited to, EDTA and deferoxamine mesylate.

A further embodiment comprises levodopa, carbidopa, a thioether and a chelator.

In one embodiment, compositions of the invention comprise levodopa, carbidopa and acid. In a further embodiment, the composition comprises levodopa, carbidopa, and an acid wherein said acid is hydrochloric, hydrobromic, sulfuric, sulfamic, phosphoric, nitric acid, maleic, fumaric, benzoic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, or benzenesulfonic acid. In another aspect of this invention, said acids are anhydrous acids.

Another embodiment comprises compositions of levodopa, carbidopa, acid and a thioether. An additional embodiment comprises compositions of levodopa, carbidopa, acid and a chelator. A further embodiment comprises levodopa, carbidopa, acid, a thioether and a chelator.

In another embodiment, compositions of the invention comprise levodopa, carbidopa and an acid:
   a. wherein said acid is hydrochloric, hydrobromic, sulfuric, sulfamic, phosphoric, nitric acid, maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, or benzenesulfonic acid; and
   b. the level of degraded carbidopa is below 0.05%, below 0.1%, below 0.2%, below 0.3%, below 0.5%, below 1%, below 2%, below 5%, or below 10% after 7 days at 25° C.

In another embodiment, compositions of the invention comprise levodopa, carbidopa and an acid:
   a. wherein said acid is hydrochloric, hydrobromic, sulfuric, sulfamic, phosphoric, nitric acid, maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, or benzenesulfonic acid;
   b. the level of degraded carbidopa is below 0.05%, below 0.1%, below 0.2%, below 0.3%, below 0.5%, below 1%, below 2%, below 5%, or below 10% after 7 days at 25° C.; and
   c. the formulation further comprises a preservative such as sodium benzoate.

In another embodiment, compositions of the invention comprise levodopa, carbidopa and acid:
   a. wherein said acid is hydrochloric, hydrobromic, sulfuric, sulfamic, phosphoric, nitric acid, maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, or benzenesulfonic acid;
   b. the level of degraded carbidopa is below 0.05%, below 0.1%, below 0.2%, below 0.3%, below 0.5%, below 1%, below 2%, below 5%, or below 10% after 7 days at 25° C.; and
   c. said carbidopa or levodopa is in the form of a salt.

In another embodiment, compositions of the invention comprise levodopa, carbidopa and acid:
   a. wherein said acid is hydrochloric, hydrobromic, sulfuric, sulfamic, phosphoric, nitric acid, maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, or benzenesulfonic acid; and
   b. wherein the pH between 1 and 10, between 1 and 8, between 2 and 8, between 2 and 6, between 2 and 4, between 2.5 and 4.5, between 2.5 and 4, between 2.5 and 3.5, between 3 and 8, between 3 and 6, between 3 and 5, between 3 and 4, between 1 and 4, between 1.5 and 3.5, between 2 and 3 or less than 5, less than 4, less than 3, less than 2.9, less than 2.8, less than 2.7, less than 2.6, less than 2.5, less than 2.4, less than 2.3, less than 2.2, less than 2.1, or less than 2.

In another embodiment, compositions of the invention comprise levodopa, carbidopa and an acid:
a. wherein said acid is hydrochloric, hydrobromic, sulfuric, sulfamic, phosphoric, nitric acid, maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, or benzenesulfonic acid; and
b. wherein the concentration of levodopa is greater than 2.5 mg/ml, greater than 3 mg/ml, greater than 4 mg/ml, greater than 5 mg/ml, greater than 6 mg/ml, greater than 7 mg/ml, greater than 8 mg/ml or greater than 10 g/ml.

In another embodiment, compositions of the invention comprise levodopa, carbidopa and an acid:
a. wherein said acid is hydrochloric, hydrobromic, sulfuric, sulfamic, phosphoric, nitric acid, maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, or benzenesulfonic acid; and
b. wherein the composition has less than 10% degradation of any active ingredients at room temperature (25 degrees C.) for 12 hours, 24 hours, 36 hours, 48 hours, one week, or one month.

In another embodiment, compositions of the invention comprise levodopa, carbidopa and an acid:
a. wherein said acid is hydrochloric, hydrobromic, sulfuric, sulfamic, phosphoric, nitric acid, maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, or benzenesulfonic acid; and
b. wherein the composition has less than 10% degradation of any active ingredients at 4 degrees C. for 12 hours, 24 hours, 36 hours, 48 hours, one week, or one month.

In one embodiment, the formulation comprises levodopa at between 1 and 5 mg/ml, carbidopa at between 0.25 and 1.25 mg/ml, an acid, and a metal chelator. In another embodiment, the formulation comprises levodopa at between 1 and 5 mg/ml, carbidopa at between 0.25 and 1.25 mg/ml, an acid, and EDTA. In another embodiment, the formulation comprises levodopa at between 1 and 5 mg/ml, carbidopa at between 0.25 and 1.25 mg/ml, citric acid, and EDTA. In a further embodiment, the formulation comprises levodopa at between 1 and 5 mg/ml, carbidopa at between 0.25 and 1.25 mg/ml, citric acid at between 3 and 10 mg/ml, and EDTA. In a still further embodiment, the formulation comprises levodopa at between 1 and 5 mg/ml, carbidopa at between 0.25 and 1.25 mg/ml, citric acid at between 3 and 10 mg/ml, and EDTA of at least 0.025 ug/ml. In one aspect of this invention, the metal chelator is a salt.

In one embodiment, the formulation comprises levodopa at between 2.5 and 5 mg/ml, carbidopa at between 0.625 and 1.25 mg/ml, an acid, and a metal chelator. In one embodiment, the formulation comprises levodopa at between 2.5 and 5 mg/ml, carbidopa at between 0.625 and 1.25 mg/ml, an acid, and EDTA. In another embodiment, the formulation comprises levodopa at between 2.5 and 5 mg/ml, carbidopa at between 0.625 and 1.25 mg/ml, citric acid, and EDTA. In a further embodiment, the formulation comprises levodopa at between 2.5 and 5 mg/ml, carbidopa at between 0.625 and 1.25 mg/ml, citric acid at between 3 and 10 mg/ml, and EDTA. In a still further embodiment, the formulation comprises levodopa at between 2.5 and 5 mg/ml, carbidopa at between 0.625 and 1.25 mg/ml, citric acid at between 3 and 10 mg/ml, and EDTA of at least 0.025 ug/ml.

In one embodiment, the formulation comprises levodopa at about 4 mg/ml, carbidopa at between about 1 mg/ml, an acid, and a metal chelator. In one embodiment, the formulation comprises levodopa at about 4 mg/ml, carbidopa at between about 1 mg/ml, an acid, and EDTA. In another embodiment, the formulation comprises levodopa at about 4 mg/ml mg/ml, carbidopa at about 1 mg/ml mg/ml, citric acid, and EDTA. In a further embodiment, the formulation comprises levodopa at about 4 mg/ml mg/ml, carbidopa at about 1 mg/ml mg/ml, citric acid at between 3 and 10 mg/ml, and EDTA. In a still further embodiment, the formulation comprises levodopa at about 4 mg/ml mg/ml, carbidopa at about 1 mg/ml mg/ml, citric acid at between 3 and 10 mg/ml, and EDTA of at least 0.025 ug/ml.

In a still further embodiment, the formulation comprises levodopa at about 4 mg/ml mg/ml, carbidopa at about 1 mg/ml mg/ml, citric acid at between 3 and 10 mg/ml, EDTA of at least 0.025 ug/ml and between 0.5 and 7% of a binder. In another embodiment, the formulation comprises levodopa at about 4 mg/ml mg/ml, carbidopa at about 1 mg/ml mg/ml, citric acid at between 3 and 10 mg/ml, EDTA of at least 0.025 ug/ml, between 0.5 and 7% of a binder, and a flavor enhancer.

Compositions of this invention can be produced by combining the different agents together and mixing. Agents of this invention are available from commercial sources. Carbidopa can be purchased from Sigma-Aldrich (2002-2003 Biochemicals and Reagents Catalog, page 368). Levodopa can be purchased from Sigma-Aldrich (2002-2003 Biochemicals and Reagents Catalog, page 693). Combinations of levodopa and carbidopa can be found in currently marketed pharmaceuticals. Methods of making levodopa and carbidopa are known in the art. Other stated agents (active and inactive) are available from commercial sources.

Dissolution of a composition of this invention in liquid can occur by any methods known in the art. In some instances, dissolution can occur by mixing, stirring, blending, or homogenizing.

Dissolution of compositions of this invention can provide significant advantages to Parkinson's disease patients. Fast dissolution of components of a composition could aid a patient who suffers from rigidity, tremors and frozen episodes. Faster dissolution can occur by altering particle size of the composition and by granulating the compositions. In one embodiment, a composition of levodopa, carbidopa, and a binder has a particle size diameter of between about 5 and 20 um. Examples of applicable binders include polyvinylpyrolidone and hydroxypropylcellulose. Compositions also obtain faster dissolution by granulation in the presence of a binder and in some embodiments an liquid. Wet granulation, as opposed to dry granulation, results in a composition with improved dissolution speed.

In one embodiment, compositions of this invention dissolve at least 3 mg/ml of levodopa in a liquid within 5 minutes. On another embodiment, compositions of this invention dissolve at least 4 mg/ml of levodopa in a liquid within 5 minutes. One suitable liquid is water.

The compositions of this invention can be packaged in a variety of ways. Compositions of this invention can be packaged in individual packets, multiuse vials, multiuse contains or containers of various sizes, configurations or materials. In one embodiment, compositions of this invention are packaged such that exposure to light is minimized.

In some embodiments, compositions of this invention specifically exclude detergents. In other embodiments, compositions of this invention can form stable formulations with only levodopa and not with a derivative of levodopa. In further embodiments, compositions of this invention can form stable formulations with only a derivative of levodopa and not with levodopa. In some embodiments, compositions of this invention comprise simple formulations of two, three or four different agents without requiring combinations of five or more agents. In other embodiments, compositions of this invention do not require any type of gelling component. Examples of gelling components are, but are not limited to, hydroxypropylmethylcellulose, polyvinylpyrrolidone, polyvinyl alcohol or gelatin.

It should be understood to those skilled in the art that various changes in the form and details described in this application may be made without departing form the scope of the invention. This invention will now be described in further detail, by way of example only, with reference to the accompanying examples.

EXAMPLES

Example 1

Solubility of Levodopa in Citrate Buffer at Varying pH and Buffer Strength

Sample Preparation

Solutions were made using Citric acid and tribasic Sodium Citrate dihydrate Initially a 1.0 M citric acid solution was made by weighing out 19.2 g Citric acid (FW 192.1) into a 100 mL volumetric flask and diluting with HPLC grade water. This was repeated with the Sodium Citrate (FW 294.1), by weighting out 29.4 g of sodium citrate in into a 100 mL volumetric flask and diluting to 100 mL with water. A series of 8 of 20 mL scintillation vials were then labeled and prepared as follows:

For 1.0 molar samples of pH 1.5 (pure citric+HCl), 2.5, 3.0, 3.5, 4.0, 4.5, 5.0, 6.0 were made. These pH adjustments were made with the sodium citrate (also 1.0 M) to keep a consistent molarity with the citrate. From these mother vials, 2 subsequent sets of solution were made for the molar concentrations 0.45 and 0.15 M. 0.45 M is for a 3:1 buffer and 0.15 M is for a 1:1 buffer. These solutions were also pH adjusted with molar equivalent solution to keep the pH value consistent throughout each dilution and after adding the levodopa. The pH was adjusted with 1N HCl or 1N NaOH as needed.

Results

| Sample name Citrate buffer | Compound Levodopa | HPLC conc mg/mL | Dilution Factor | Conc mg/mL |
|---|---|---|---|---|
| 1.0M pH 1.5 | Levodopa | 0.239 | 75 | 17.93 |
| 1.0M pH 2.5 | Levodopa | 0.619 | 12 | 7.43 |
| 1.0M pH 3.0 | Levodopa | 0.741 | 8 | 5.93 |
| 1.0M pH 3.5 | Levodopa | 0.654 | 8 | 5.23 |
| 1.0M pH 4.0 | Levodopa | 0.93 | 5 | 4.65 |
| 1.0M pH 4.5 | Levodopa | 0.887 | 5 | 4.44 |
| 1.0M pH 5.0 | Levodopa | 0.833 | 5 | 4.17 |
| 1.0M pH 6.0 | Levodopa | 0.773 | 5 | 3.87 |
| 0.45M pH1.5 | Levodopa | 0.152 | 75 | 11.40 |
| 0.45M pH2.5 | Levodopa | 0.485 | 12 | 5.82 |
| 0.45M pH3.0 | Levodopa | 0.606 | 8 | 4.85 |
| 0.45M pH3.5 | Levodopa | 0.564 | 8 | 4.51 |
| 0.45M pH4.0 | Levodopa | 0.849 | 5 | 4.25 |
| 0.45M pH4.5 | Levodopa | 0.85 | 5 | 4.25 |
| 0.45M pH5.0 | Levodopa | 0.829 | 5 | 4.15 |
| 0.45M pH6.0 | Levodopa | 0.832 | 5 | 4.16 |
| 0.15M pH1.5 | Levodopa | 0.096 | 75 | 7.20 |
| 0.15M pH2.5 | Levodopa | 0.406 | 12 | 4.87 |
| 0.15M pH3.0 | Levodopa | 0.526 | 8 | 4.21 |
| 0.15M pH3.5 | Levodopa | 0.488 | 8 | 3.90 |
| 0.15M pH4.0 | Levodopa | 0.758 | 5 | 3.79 |
| 0.15M pH4.5 | Levodopa | 0.776 | 5 | 3.88 |
| 0.15M pH5.0 | Levodopa | 0.776 | 5 | 3.88 |
| 0.15M pH6.0 | Levodopa | 0.789 | 5 | 3.95 |

Example 2

Stability of Levodopa and Carbidopa

Sample Preparation:

A formulation of: Levodopa/Citric acid/Carbidopa/Sucrose mix at molar ratio of 1:3:0.2:1. This powder mixture was dissolved in water at a concentration of 5.5 mg/ml of levodopa. This solution was filter through a 0.22 micrometer filter (with PVDF membrane) and then stored at temperatures of 4 degrees C., 25 degrees C. and 40 degrees C.

A formulation of Levodopa/Ascorbic acid/Carbidopa mix at molar ratio of 1:3:0.25. This powder mixture was dissolved in water at concentration of 1.0 mg/ml of levodopa. This solution was filtered through a 0.22 micrometer filter (with PVDF membrane) and then stored at temperatures of 4 degrees C., 25 degrees C. and 40 degrees C.

The sample solutions were submitted for HPLC potency test at each time point. The stability was monitored in percentage change compared to the initial potency.

| Sample name | Compound | Initial | 1 Day | 2 Day | 3 Day | 7 Day |
|---|---|---|---|---|---|---|
| Levodopa/Citric/Carbidopa/Sucrose at 1/3/0.2/1 at 4 C. | Levodopa | 100% | 100% | 100% | 100% | 100% |
| | Carbidopa | 100% | 100% | 100% | 101% | 100% |
| Levodopa/Citric/Carbidopa/Sucrose at 1/3/0.2/1 at 25 C. | Levodopa | 100% | 100% | 100% | 100% | 100% |
| | Carbidopa | 100% | 98% | 96% | 96% | 91% |
| Levodopa/Citric/Carbidopa/Sucrose at 1/3/0.2/1 at 40 C. | Levodopa | 100% | 100% | 100% | 100% | 100% |
| | Carbidopa | 100% | 91% | 84% | 81% | 75% |
| Levodopa/Ascorbic/Carbidopa/at 1/3/0.2 at 4 C. | Levodopa | 100% | 100% | 100% | NA | 102% |
| | Carbidopa | 100% | 101% | 101% | NA | 101% |
| Levodopa/Ascorbic/Carbidopa/at 1/3/0.2 at 25 C. | Levodopa | 100% | 100% | 100% | NA | 102% |
| | Carbidopa | 100% | 99% | 97% | NA | 87% |
| Levodopa/Ascorbic/Carbidopa/at 1/3/0.2 at 40 C. | Levodopa | 100% | 100% | 101% | NA | 104% |
| | Carbidopa | 100% | 94% | 88% | NA | 88% |

Example 3

Carbidopa Degradant

Samples of levodopa/carbidopa/citric acid and levodopa/carbidopa/ascorbic acid at a molar ratio of 4:1:1 were made. Samples were kept at 25 degrees Celsius for 24 hours. After 24 hours, samples were assayed on an HPLC. Analysis was carried out on Waters Alliance HPLC system equipped with 2695 separation module and 2996 PDA detector. Reversed phase HPLC method was utilizing Waters Atlantis dC18 column (4.6×150 mm, 5 um) operated at 30 C and a two component gradient mobile phase. Run time was 30 min at flow rate 1.0 mL/min. Levodopa and carbidopa impurities and degradation products were detected by absorbance at 280 nm and reported as their percent area relative to the parent peak. A new peak was determined to be 3,4-dihydroxyphenylacetone by HPLC/MS. 3,4-dihydroxyphenylacetone (DHPA) is a carbidopa degradant. This degradant is also present in formulations of levodopa/carbidopa/orange juice and in formulations of levodopa/carbidopa/ginger ale.

Example 4

Stability of Levodopa and Carbidopa Formulations

Formulations of levodopa, carbidopa and an acid at various pHs were tested for carbidopa stability. Four grams of levodopa and one gram of carbidopa were dissolved with 3 Molar equilavents of various acids relative to levodopa and water as shown in the table below. The pH of each solution was adjusted 1 N HCl or 1 N NaOH. Area levodopa, area carbidopa, % carbidopa remaining and area % of DHPA were calculated.

The "% carbidopa remaining was calculated according to the following equations:

$$\text{Carb}_{4C}\text{theoretical} = \text{carb}_{4C} * \text{lev}_T / \text{lev}_{4C}$$

$$\text{"\% carb remaining"} = \text{carb}_T / \text{carb}_{4C}\text{theoretical} * 100$$

where $\text{carb}_T$ and $\text{Lev}_T$ refer to carbidopa and levodopa area values for the acid, temperature, and pH being studied, and $\text{lev}_{4C}$ and $\text{carb}_{4C}$ are the area values of the levodopa and carbidopa samples at 4° C. for the pH and acid being studied.

| Acid | pH | ° C. | area levodopa | area carbidopa | % carb remaining | area % DHPA |
|---|---|---|---|---|---|---|
| Acetic acid | 2 | 4 | 2864780 | 556275 | 100.0 | 0 |
| | | 25 | 2920134 | 562629 | 99.2 | 1.14 |
| | | 40 | 2927442 | 555971 | 97.8 | 2.29 |
| | 2.4 | 4 | 1255379 | 297891 | 100.0 | 0 |
| | | 25 | 3007344 | 589068 | 82.5 | 0.93 |
| | | 40 | 2952343 | 565106 | 80.7 | 3.13 |
| | 3 | 4 | 2861179 | 596623 | 100.0 | 0 |
| | | 25 | 2883225 | 592870 | 98.6 | 1.51 |
| | | 40 | 2573780 | 493081 | 91.9 | 3.92 |
| Citric acid | 2 | 4 | 3142973 | 603604 | 100.0 | 0 |
| | | 25 | 3133573 | 591206 | 98.2 | 1.83 |
| | | 40 | 2960941 | 566867 | 99.7 | 0.75 |
| | 2.4 | 4 | 3108393 | 597902 | 100.0 | 0 |
| | | 25 | 3122562 | 599299 | 99.8 | 0.71 |
| | | 40 | 3181927 | 600710 | 98.1 | 1.73 |
| | 3 | 4 | 2986595 | 571393 | 100.0 | 0.92 |
| | | 25 | 3108402 | 589580 | 99.1 | 1.21 |
| | | 40 | 3111696 | 577629 | 97.0 | 2.85 |
| HCl | 2 | 4 | 2956816 | 572525 | 100.0 | 0 |
| | | 25 | 2943735 | 567786 | 99.6 | 0.84 |
| | | 40 | 3003245 | 568938 | 97.8 | 2.28 |
| | 2.4 | 4 | 3014797 | 581503 | 100.0 | 0.80 |
| | | 25 | 2837880 | 545321 | 99.6 | 1.15 |
| | | 40 | 2947773 | 549080 | 96.6 | 3.30 |
| | 3 | 4 | 2907279 | 558606 | 100.0 | 0.99 |
| | | 25 | 2837293 | 540713 | 99.2 | 1.56 |
| | | 40 | 2818351 | 512352 | 94.6 | 4.96 |
| L-(−)-Malic acid | 2 | 4 | 3139874 | 604922 | 100.0 | 0.62 |
| | | 25 | 3091146 | 592188 | 99.4 | 0.90 |
| | | 40 | 3121877 | 587787 | 97.7 | 2.22 |
| | 2.4 | 4 | 3114444 | 602433 | 100.0 | 0.57 |
| | | 25 | 3007871 | 578488 | 99.4 | 0.90 |
| | | 40 | 3049661 | 577045 | 97.8 | 2.21 |
| | 2.6 | 4 | 3061962 | 595963 | 100.0 | 0.53 |
| | | 25 | 2879955 | 557074 | 99.4 | 0.85 |
| | | 40 | 3121864 | 582676 | 95.9 | 2.22 |
| L-(+)-Tartaric acid | 2 | 4 | 3137768 | 598319 | 100.0 | 0.53 |
| | | 25 | 3323491 | 622853 | 98.3 | 1.71 |
| | | 40 | 3037389 | 499461 | 86.2 | 10.22 |
| | 2.4 | 4 | 3164710 | 598138 | 100.0 | 0.64 |
| | | 25 | 3191366 | 589671 | 97.8 | 1.94 |
| | | 40 | 3165751 | 512299 | 85.6 | 11.36 |
| | 3 | 4 | 3042627 | 573035 | 100.0 | 0.96 |
| | | 25 | 2932384 | 537924 | 97.4 | 2.37 |
| | | 40 | 3080403 | 508334 | 87.6 | 9.15 |
| Malonic acid | 2 | 4 | 3198987 | 618183 | 100.0 | 0.44 |
| | | 25 | 2956945 | 564456 | 98.8 | 0.76 |
| | | 40 | 3091218 | 581615 | 97.4 | 2.16 |
| | 2.4 | 4 | 2928983 | 561988 | 100.0 | 0.64 |
| | | 25 | 3194883 | 609472 | 99.4 | 1.13 |
| | | 40 | 3123140 | 588045 | 98.1 | 2.36 |
| | 3 | 4 | 3060381 | 585961 | 100.0 | 0.84 |
| | | 25 | 3027405 | 573498 | 98.9 | 1.62 |
| | | 40 | 3040114 | 560576 | 96.3 | 3.63 |
| $H_3PO_4$ | 2 | 4 | 3043106 | 580763 | 100.0 | 0.50 |
| | | 25 | 3121711 | 592491 | 99.5 | 0.76 |
| | | 40 | 2920381 | 546560 | 98.1 | 1.83 |
| | 2.4 | 4 | 3076836 | 585580 | 100.0 | 0.63 |
| | | 25 | 2741837 | 519759 | 99.6 | 0.70 |
| | | 40 | 3042791 | 566757 | 97.9 | 2.06 |
| | 3 | 4 | 3016323 | 574096 | 100.0 | 0.58 |
| | | 25 | 2827873 | 533847 | 99.2 | 0.84 |
| | | 40 | 2828586 | 516553 | 95.9 | 3.27 |
| Succinic acid | 2 | 4 | 2967669 | 586937 | 100.0 | 0.77 |
| | | 25 | 3062470 | 602825 | 99.5 | 1.20 |
| | | 40 | 3107285 | 594742 | 96.8 | 3.19 |
| | 2.4 | 4 | 2991187 | 592581 | 100.0 | 0.72 |
| | | 25 | 2969082 | 584084 | 99.3 | 1.22 |
| | | 40 | 2921618 | 559184 | 96.6 | 3.28 |
| | 3 | 4 | 2905509 | 621872 | 100.0 | 0.91 |
| | | 25 | 3003987 | 603028 | 93.8 | 1.54 |
| | | 40 | 3059716 | 579495 | 88.5 | 4.10 |
| Sulfuric acid | 2 | 4 | 2434399 | 491414 | 100.0 | 0.89 |
| | | 25 | 2163586 | 432313 | 99.0 | 1.14 |
| | | 40 | 2303265 | 444509 | 95.6 | 3.83 |
| | 2.4 | 4 | 2175680 | 435950 | 100.0 | 1.02 |
| | | 25 | 2210814 | 440745 | 99.5 | 1.32 |
| | | 40 | 2324408 | 448587 | 96.3 | 4.14 |
| | 3 | 4 | 2232850 | 442564 | 100.0 | 1.46 |
| | | 25 | 2187525 | 430200 | 99.2 | 2.05 |
| | | 40 | 2303472 | 425755 | 93.3 | 6.98 |

This data suggest a selection of a particular acid is important in a liquid formulation of levodopa and carbidopa. It is possible that combinations of these different acids could create a more stable liquid formulation.

Example 5

Ratio of Carbidopa to Levodopa

Samples if 1/3/1 Levodopa/citric acid/sucrose were prepared at 4 mg/ml of levodopa and carbidopa was added at w/w ratios of 0.5, 0.125, and 0.05 relative to levodopa. The samples were diluted for HPLC analysis after 24 hours at 4 C, 25 C, and 40 C.

Area % DHPA relative to carbidopa area as a function of temperature and levodopa/carbidopa ratio.

|  | 0.50 w/w carb/l-dopa | 0.125 w/w carb/l-dopa | 0.05 w/w carb/l-dopa |
|---|---|---|---|
| 4° C. | 0.60 | 0.57 | 0.00 |
| 25° C. | 0.97 | 0.73 | 0.00 |
| 40° C. | 2.45 | 1.76 | 1.51 |

The data indicates that the ratio of carbidopa to levodopa effects affects carbidopa stability.

Example 6

Stability of Levodopa and Carbidopa in Ginger Ale

The stability of a formulation of levodopa and carbidopa was tested with ginger ale. A formulation of 4 mg/ml of levodopa and 1 mg/ml of carbidopa was combined with 100 ml of ginger ale. The formulation was kept at 4° C., 25° C. and 40° C. for 24 hours. After 24 hours the samples were diluted and assayed by HPLC. The HPLC sample chamber was maintained at 5° C. Analysis was carried out on Waters Alliance HPLC system equipped with 2695 separation module and 2996 PDA detector. Reversed phase HPLC method was utilizing Waters Atlantis dC18 column (4.6×150 mm, 5 um) operated at 30 C and a two component gradient mobile phase. Run time was 30 min at flow rate 1.0 mL/min. Levodopa and carbidopa impurities and degradation products were detected by absorbance at 280 nm and reported as their percent area relative to the parent peak.

Ginger Ale has two main peaks at RT=11.2 min and 19.3 min with lambda max values of 285 and 229.7 nm, respectively. The following table shows the amount of the 3,4-dihydroxyphenylacetone degradate formed after 24 hours. Carbidopa degrades to 3,4-dihydroxyphenylacetone. Thus, measuring this degradate is a measure of carbidopa stability.

|  | Temp | | |
|---|---|---|---|
|  | 4° C. | 25° C. | 40° C. |
| DHPA | 6.3 | 24.4 | 57.6 |

A significant level of carbidopa had degraded at 24 hours at 25° C. and 40° C. There are additional smaller degradates at RT 9.77 min (constant amount at 5° C. and 25° C.) and at RT=14.27 min.

Example 7

Effect of Ionic Strength

A formulation of Levodopa/carbidopa/citric acid/sucrose at a molar ratio of 1/0.25/3/1 was prepared at 4 mg/ml of levodopa in NaCl solution with [NaCl] of 0.00, 0.05, 0.125, 0.250, and 0.5 M. After 24 hours the samples were diluted and assayed by HPLC (as described earlier). The HPLC sample chamber was maintained at 5° C. Area % 3, 4-dihydroxyphenylacetone relative to carbidopa area as a function of temperature and ionic strength is shown as a representation of carbidopa stability.

|  | 0 M NaCl | 0.05 M | 0.125 M | 0.25 M | 0.5 M |
|---|---|---|---|---|---|
| 4° C. | 0.53 | 0.64 | 0.54 | 0.61 | 0.50 |
| 25° C. | 0.72 | 0.81 | 0.89 | 0.84 | 0.88 |
| 40° C. | 2.08 | 2.17 | 2.17 | 2.44 | 2.64 |

Salt appears to have a negative impact on carbidopa stability, which could be due to heavy metal contaminants in the salt.

Example 8

Effect of pH on Stability

Samples of carbidopa and citric acid were made. Samples were kept at 4° C., 25° C. and 40° C. for 24 hours. After 24 hours the samples were diluted and assayed by HPLC. Analysis was carried out on Waters Alliance HPLC system equipped with 2695 separation module and 2996 PDA detector. Reversed phase HPLC method was utilizing Waters Atlantis dC18 column (4.6×150 mm, 5 um) operated at 30 C and a two component gradient mobile phase. Run time was 30 min at flow rate 1.0 mL/min. Carbidopa impurities and degradation products were detected by absorbance at 280 nm and reported as their percent area relative to the parent peak.

The HPLC sample chamber was maintained at 5° C. Area % 3.4-dihydroxyphenylacetone relative to carbidopa area as a function of temperature and pH is shown as a representation of carbidopa stability.

|  | 4 C. | 25 C. | 40 C. |
|---|---|---|---|
| pH 2.0 | 0.85 | 2.40 | 8.78 |
| pH 2.5 | 0.99 | 3.60 | 11.83 |
| pH 3.0 | 1.25 | 3.92 | 10.60 |
| pH 4.0 | 1.74 | 22.51 | 45.33 |
| pH 5.5 | 7.92 | No data | 44.65 |

The results indicate that lowering the pH of the formulation increases stability of carbidopa.

Samples of 1/0.25/3/1 Levodopa/carbidopa/citric acid/sucrose were prepared at 4.0 mg/ml of levodopa in water, and the pH of the solution was adjusted to values of 1.8, 2.0, 2.2, 2.4, 2.6, 2.8, 3.0, and 3.2 with HCl or NaOH as needed. Three aliquots of each solution were transferred into vials, which were stored at 4° C., 25° C., and 40° C. After 24 hours the samples were diluted and assayed by HPLC. Area % 3, 4-dihydroxyphenylacetone relative to carbidopa area as a function of temperature and pH is shown as a representation of carbidopa stability.

| pH | 4° C. | 25° C. | 40° C. |
|---|---|---|---|
| 1.8 | — | 0.53 | 1.77 |
| 2.0 | undetectable | 0.53 | 2.02 |
| 2.2 | undetectable | 0.57 | 1.99 |
| 2.4 | undetectable | 0.68 | 2.34 |
| 2.6 | undetectable | 0.82 (0.82) | 2.46 |
| 2.8 | undetectable | — (1.21) | 2.83 |
| 3.0 | undetectable | — (2.02) | 4.62 |
| 3.2 | undetectable | — (2.43) | 6.38 |

Example 9

Effect of Sugar on Stability

Effect of sugars on the formation of DHPA over 24 hours for samples of 4 mg/ml levodopa+1 mg/ml carbidopa+3 equiv of citric acid (relative to levodopa) stored at 4, 25, and 40° C. Values reported are "area % DHPA" relative to carbidopa.

|  | 4 C. | 25 C. | 40 C. |
|---|---|---|---|
| no sugar | 0 | 0.39 | 1.53 |
| 0.5 equiv sucrose | 0 | 0.38 | 1.69 |
| 1.0 equiv sucrose | 0 | 0.51 | 1.94 |
| 1.0 equiv fructose | 0 | 0.56 | 2.27 |
| 1.0 equiv glucose | 0 | 0.52 | 2.39 |

There is no measurable degradation at 4 C. Samples with no sugar are indistinguishable from those with 0.5% sucrose after 24 hours at RT, but the sugar-free formulation has an advantage at 40 C. The amount of degradation increases with increasing sucrose concentration. A corresponding effect could occur with other aldehydes or ketones.

Example 10

Effect of Preservatives on Stability

Samples of 1/0.25/3/1 Levodopa/carbidopa/citric acid/sucrose were prepared at 5.0 mg/ml of levodopa in water and the preservatives sodium benzoate and potassium sorbate were added to the solutions. The preservatives were added at the maximum allowable concentration of 0.1% each. The solutions were placed on stability for 24 hours and assayed by HPLC. Analysis was carried out on Waters Alliance HPLC system equipped with 2695 separation module and 2996 PDA detector. Reversed phase HPLC method was utilizing Waters Atlantis dC18 column (4.6×150 mm, 5um) operated at 30° C. and a two component gradient mobile phase. Run time was 30 min at flow rate 1.0 mL/min. Levodopa and carbidopa impurities and degradation products were detected by absorbance at 280 nm and reported as their percent area relative to the parent peak.

In the 25° C. potassium sorbate samples, a new peak at RT=17.54 min was observed. The peak has a λmax value of 321.9. The area % value of the peak is 0.04%. The peak is also present at the same size when a combination of sodium benzoate and potassium sorbate is used. It is not present in samples that do not contain any potassium sorbate. After 24 hours at 40° C., the peak accounts for 0.19% of the area.

Placebos were prepared in order to determine whether the new peak is related to the potassium sorbate itself or from an interaction between potassium sorbate and levodopa or carbidopa. The first placebo was potassium sorbate in water stored at 4° C., 25° C., and 40° C. for 24 hours. There is a broad hump around RT=17.5 min in the 4° C. sample, but it almost disappears at 25° C. and returns partially at 40° C. The second placebo contains 14.5 mg/ml of citric acid and ⅓ molar equivalents of sucrose (relative to citric acid). The RT=17.5 min peak is not present in this sample at any of the temperatures studied.

No observable interaction occurs between levodopa or carbidopa and sodium benzoate. At least one new degradant is formed at RT=17.5 min when potassium sorbate is combined with levodopa and carbidopa.

The impact of each preservative on the area % of the 3,4-dihydroxyphenylacetone degradate was evaluated. No detectable 3,4-dihydroxyphenylacetone was present in the 4° C. samples. At 25° C., sodium benzoate had no effect to a slightly negative effect on the area % of 3,4-dihydroxyphenylacetone (0.71% with vs 0.88% without), while the size of the degradate doubled in the sample containing potassium sorbate. The trend held at 40° C. with no preservative giving 2.69 area %, sodium benzoate giving 2.89%, and potassium sorbate leading to 10.7% conversion of carbidopa to 3,4-dihydroxyphenylacetone.

Thus, potassium sorbate increases the rate of 3,4-dihydroxyphenylacetone formation over preservative-free or sodium benzoate-containing solutions.

Example 11

Effect of Citric Acid Concentration

The effects of citric acid content and a HCl salt of levodopa on the rate of carbidopa degradation to 3,4-dihydroxyphenylacetone were analyzed. Samples of levodopa HCl salt or free form levodopa at 4 mg/ml, carbidopa at 1 mg/ml and sucrose at 4 mg/ml were made. As detailed in the chart below, between 0 and 3 equivalents of citric acid (in relation to levodopa) were added. Effects of citric acid concentration on the 24 hour stability of carbidopa were analyzed by looking for formation of 3,4-dihydroxyphenlacetone. The below table list DHPA Area %.

| Effect of citric acid concentration with L-dopa HCl | | | |
|---|---|---|---|
| equiv of citric acid | 4° C. | 25° C. | 40° C. |
| 0 | 0 | 1.08 | 5.95 |
| 0.5 | 0 | 0.74 | 3.95 |
| 1 | 0 | 0.6 | 3.87 |
| 2 | 0 | 0.8 | 3.59 |
| Effect of citric acid concentration with L-dopa | | | |
| equiv cit | 4° C. | 25° C. | 40° C. |
| 0 | 1.32 | 12.8 | 24.1 |
| 0.5 | 0.41 | 1.01 | 3.89 |
| 1 | 0.24 | 0.75 | 2.82 |
| 2 | 0.23 | 0.84 | 2.45 |
| 3 | 0.3 | 0.75 | 2.26 |

The procedure was repeated as above with the free form of levodopa with the formulation lacking sucrose.

| Effect of citric acid concentration on the 24 hour stability of 1/0.25 weight ratio L-dopa/carbidopa: area % of DHPA formed. | | | |
|---|---|---|---|
| equiv of citric acid | 4° C. | 25° C. | 40° C. |
| 1 | 0.32 | 0.64 | 2.08 |
| 1.3 | 0.2 | 0.57 | 1.9 |
| 1.6 | 0.2 | 0.53 | 2.07 |
| 2 | 0.28 | 0.52 | 1.79 |

This data demonstrates that increasing levels of citric acid results in an increased stability of carbidopa. In addition, the HCl salt of levodopa increases stability of the carbidopa.

Example 12

An assay was developed to test solutions for hydrazine. A series of solutions with no amount of hydrazine were tested. The following data and plot shows that there is a linear correlation between the UV absorption and the amount of hydrazine in ppm between 0.27 ppm and 13.5 ppm

| Hydrazine in ppm | UV absorption |
| --- | --- |
| 13.5 | 0.32 |
| 2.7 | 0.063 |
| 1.35 | 0.033 |
| 0.27 | 0.007 |

This hydrazine assay protocol has detection limitation of hydrazine at level of 0.27 ppm when 0.10 ml of sample was assayed. The sample size was increased to 0.50 ml in order to decrease the lower limit of the quantitation to below 0.10 ppm. The limit of detection of the larger sample volume is 0.05 ppm. The following data indicated a linear correlation between UV absorption and volume of tested sample solution.

| Correlation between UV Absorption and Volume of Tested Solution | | | | |
| --- | --- | --- | --- | --- |
| | Hydrazine standard solution | | | |
| | 0.27 ppm | 0.27 ppm | 0.05 ppm | 0.05 ppm |
| | Volume of sample solution | | | |
| | 0.1 ml | 0.2 ml | 0.5 ml | 1.0 ml |
| UV reading #1 | 0.006 | 0.011 | 0.006 | 0.011 |
| UV reading #2 | 0.006 | 0.011 | 0.006 | 0.011 |
| UV reading #3 | 0.005 | 0.011 | 0.006 | 0.011 |

It is believed that carbidopa is the source of hydrazine formation in the levodopa/carbidopa formulation solutions. It is believed that DHPA is the main degradant of carbidopa in acidic solution, and a co-product of hydrazine formation. DHPA can be detected by HPLC assay. The following data indicated that there is a good correlation between the % of DHPA and the amount of hydrazine in ppm.

| TPI-leading formulation | | Correlation ratio |
| --- | --- | --- |
| % DHPA | Hydrazine (ppm) | % DHPA/ppm of Hydrazine |
| 0.5 | 0.433 | 1.154 |
| 0.8 | 0.788 | 1.016 |
| 0.95 | 0.906 | 1.049 |
| 1.7 | 1.457 | 1.167 |

Several levedopa/carbidopa formulation solutions have been tested with both HPLC assay and hydrazine assay.

| Levedopa/Carbidopa Formulation Solutions 24 Hours at 25° C. | % DHPA | Hydrazine in ppm |
| --- | --- | --- |
| SINEMET/Ascorbic solution | 0.40 | 0.33 |
| Levedopa/Carbidopa solution at 4:1 ratio | 0.51 | 0.41 |
| Levedopa/Carbidopa solution at 4:1 ratio + Cystine | 0.28 | |
| Levedopa/Carbidopa solution at 4:1 ratio + Metionine | 0.31 | |
| Levedopa/Carbidopa solution at 4:1 ratio + Metionine + deferoxamine | 0.15 | |
| Levedopa/Carbidopa solution at 4:1 ratio + Cystine + EDTA | 0.00 | 0.00 |
| Levedopa/Carbidopa solution at 4:1 ratio + Cystine + deferoxamine | 0.00 | 0.00 |
| Levedopa/Carbidopa solution at 4:1 ratio + Metionine + EDTA | 0.00 | 0.00 |

This data demonstrates that thioethers and chelators can be used to decrease hydrazine presence in formulations of levodopa and carbidopa.

Example 13

Formulations of TPI-926 were compared to Parkinson's disease patient's current off-label practice of making liquid levodopa and carbidopa drinks. TPI-926 contains:
4 mg/ml of levodopa
1 mg/ml of carbidopa
7.8 mg/ml Citric acid
0.1 mg/ml Na EDTA
0.5 mg/ml of aspartame The total volume of TPI-926 was 100 ml of water. Liquid formulations of levodopa at 1 mg/ml and carbidopa at 0.25 mg/ml were made in orange juice and ginger ale by grinding 1 levodopa/carbidopa tablet (100:25) and combining with 100 ml of orange juice or ginger ale. A formulation of levodopa, carbidopa and ascorbic acid was made by grinding 1 levodopa/carbidopa tablet (100:25) and combining with 100 ml of water and 2 mg/ml of ascorbic acid.

Samples were kept at 4 and 25 degrees C. for 24 hours, 3 days, and 7 days. Samples were analyzed for hydrazine and DHPA content by HPLC.

DHPA is a degradant of carbidopa. Thus, DHPA is at a 1:1 ratio compared to degraded carbidopa. A 1% level of DHPA in a sample is expected to correlate with a 1% level of carbidopa degradation.

The concentration per day was calculated by dividing the amount of hydrazine or DHPA of the longest duration sample divided by the number of days.

Hydrazine (mcg/sample) at 4 Degrees C.

| | 1 day | 3 days | 7 days | Per Day |
| --- | --- | --- | --- | --- |
| '926 | <1.5 | <1.5 | 1.5 | 0.2 |
| ascorbic in H2O | <6.0 | <6.0 | 6.2 | 0.9 |
| OJ | 7.3 | 10.1 | n.m. | |
| Ginger ale | 21.2 | 121.5 | n.m. | 40.5 |

Hydrazine (mcg/sample) at 25 Degrees C.

| | 1 day | 3 days | 7 days | Per Day |
| --- | --- | --- | --- | --- |
| '926 | <1.5 | 2.6 | 5.6 | 0.8 |
| ascorbic in H2O | 7.3 | 32.5 | 160.3 | 23 |
| OJ | 24.1 | 37.1 | n.m. | |
| Ginger ale | 253 | 765 | n.m. | 255 |

| DHPA (mcg/sample) at 25 degrees C. | | | | |
| --- | --- | --- | --- | --- |
| | 1 day | 3 days | 7 days | Per Day |
| '926 | <25.0 | <25.0 | 25.6 | 3.7 |
| Ascorbic in $H_2O$ | 81 | 346 | 1704 | 238 |
| Ginger ale | 3210 | 9038 | | 3013 |

This data demonstrates that TPI-926 prevents or decreases formation of hydrazine at both 4 and 25 degrees C.

Percent Carbidopa loss was calculated. By converting the total mcg of DHPA to mcg of carbidopa.
TPI-926

100 ml of TPI-926 created 3.7 mcg of DHPA per day. Since DHPA and carbidopa are in molar equivalents, this correspond with 5 mcg of carbidopa degradation per day. One tablet of SINEMET contains 25,000 mcg of carbidopa. Thus, TPI-926 has a 0.02% degradation rate of carbidopa per day for every 250 mg.

Levodopa/carbidopa and Ascorbic Acid in Water 100 ml of the ascorbic acid sample created 238 mcg of DHPA per day. Since DHPA and carbidopa are in molar equilavents, this correspond with 323 mcg of carbidopa degradation per day. One tablet of SINEMET contains 25,000 mcg of carbidopa.

Thus, ascorbic acid sample has a 1.2% degradation rate of carbidopa per day for every 250 mg dose.

Levodopa/Carbidopa in Ginger Ale 100 ml of the ginger ale sample created 3013 mcg of DHPA per day. Since DHPA and carbidopa are in molar equivalents, this correspond with 4083 mcg of carbidopa degradation per day. One tablet of Sinemet contains 25,000 mcg of carbidopa. Thus, this ginger ale sample has a 16.3% degradation rate of carbidopa per day for every 250 mg.

Example 14

Levedopa solubility in ascorbic acid solution an ascorbic acid concentration of 3.5 mg/ml was tested. A sample of 3.5 mg/ml ascorbic acid was made by adding 70.0 mg of ascorbic acid into 20 ml of water. Then, 80.0 mg of levodopa powder was dissolved into the 3.5 mg/ml ascorbic sample by stirring for 24 hour at RT. The projected levodopa concentration was 4 mg/ml. The sample was filtered through a 0.22μ PVDF filter to remove the insoluble levodopa. The filtration was assayed by HPLC at 10× dilution with water. The HPLC data indicated the concentration of levodopa in the filtration was 2.0 mg/ml. Thus, maximum solubility of levodopa in 3.5 mg/ml ascorbic acid solution was 2 mg/ml.

Example 15

A formulation of levodopa and carbidopa with low levels of metal ions was made. A formulation of:

Levodopa 4 mg/ml
Carbidopa 1 mg/ml
Hydrogen chloride 0.02 Normal
EDTA-Na dihydrate 0.11 mg/ml
Saccharin 0.5 mg/ml
Sodium Benzoate 0.10 mg/ml
Deionized water to 1 ml A deionization procedure with a cation removal cartridge (Hose Nipple Cartridge D8905 from Barnstead International) was utilized for water purification. After all components were dissolved in the purified water, a dialysis step with Chelex-100® was conducted. The pH of the solution was adjusted to within 2.0~2.3. The level of carbidopa degradation was measured for this formulation. At time 0, 0.125% of carbidopa had degraded. After two weeks at room temperature (25° C.) 0.196% carbidopa had degraded. After one month at room temperature, 0.233% carbidopa had degraded. After two weeks at 40° C., 0.618% carbidopa had degraded. After one month at 40° C., 1.276% carbidopa had degraded.

Example 16

Rate of formulation dissolution was tested. Levodopa as purchased has a mean particle size of 76 um, where 50% of the particles are less than 67 um, 90% of the particles are less than 146 um, and 100% of the particles are less than 364 um. Using the a solid formulation of:
Levodopa 100 mg
Carbidopa 27 mg
Citric acid monohydrate 213 mg
EDTA-NA dihydrate 2.75 mg
Aspartame 12.5 mg
Sodium Benzoate 2.5 mg And levodopa with the above particle ranges, complete levodopa dissolution did not occur within 24 hours in deionized water. Method of mixing the formulation components was shaking.

The same formulation was used except the levodopa was replaced with levodopa with a mean particle size of 5.5 um, where 50% of the particles are less than 5.11 um, 90% of the particles are less than 10.4 um, and 100% of the particles are less than 19.4 um (the I1 particle size batch). Another formulation was tested with a mean particle size of 17.3 um, where 50% of the particles are less than 13.95 um, 90% of the particles are less than 37 um, and 100% of the particles are less than 78 um (the 16 particle size batch). The 19 batch was granulated by manual grinding with water. This formulation had complete dissolution within 1 hour. Addition of polyvinylpyrolidone and ethanol also improved dissolution as shown below.

| Expt. ID | TPI-926 mill cut | Binder | Method of Addition | Liquid | Citric Acid Addition | 90% TPI-926 disso* | Complete disso |
|---|---|---|---|---|---|---|---|
| 1 | I1 | — | — | Water | In granules | <1 min | >1 hr* (*significant < 1 hr) |
| 4 | I1 | PVP | 5% solid | EtOH | In granules | <1 min | ~10 min |
| 3 | I1 | PVP | 5% solid | EtOH | Blended w/granules | <1 min | ~5 min |
| A | I1 | PVP | 5% solid | EtOH | Blended w/granules | <1 min | ~5 min |
| B | I6 | PVP | 5% solid | EtOH | Blended w/granules | <4 min | >1 hr* (*significant ~10 min) |
| C | I1 | PVP | 10% soln | EtOH | Blended w/granules | <1 min | ~5 min |

A particle size of between 7 and 13 um showed fast dissolution. The addition of a binder such as polyvinylpyrollidone or hydroxypropylcellulose increase dissolution speed.

Example 17

Chelation of Heavy Metal Ions by Addition of EDTA EDTA (at 0.9 mg/ml as the sodium salt) was added to a formulation (levodopa at 4 mg/ml, carbidopa at 1 mg/ml, citric acid at 7.79 mg/ml, aspartame at 0.5 mg/ml, sodium benzoate at 0.25 mg/ml) with and without the addition of iron (Fe(III) citrate at 0.3 ppm) and copper ($CuSO_4$ at 1 ppm). The metal concentrations were chosen to match those of the EPA secondary guideline for drinking water. The measured pH of all solutions at the initial time was 2.67±0.05. Area % DHPA values are reported relative to carbidopa area. As described earlier, % DHPA correlates with carbidopa degradation and hydrazine formation. The samples were stored at 25° C. for 20 hours and assayed using HPLC.

| Metal | % DHPA with no EDTA | % DHPA with EDTA |
|---|---|---|
| Fe | 0.893 | 0.202 |
| Cu | 0.640 | 0.181 |
| No Metal | 0.474 | 0.189 |

These results demonstrate that metal ions function to accelerate carbidopa degradation and that metal chelators can slow or inhibit this action.

The invention claimed is:

1. A pharmaceutical dosage form comprising an aqueous solution of levodopa, carbidopa, an acid, and a metal chelator, wherein the levodopa concentration is up to about 30 mg/ml, the molar ratio of levodopa to carbidopa is 3:1 to 25:1, and the solution exhibits a 7 day, 25° C. carbidopa degradation rate of less than 5%.

2. The pharmaceutical dosage form of claim 1, wherein the aqueous solution has a pH less than 3.

3. The pharmaceutical dosage form of claim 1, wherein the metal chelator is selected from the group consisting of EDTA, deferoxamine mesylate, EGTA, fumaric acid, and malic acid, or salts thereof.

4. The pharmaceutical dosage form of claim 1, wherein the metal chelator comprises EDTA or salts thereof.

5. The pharmaceutical dosage form of claim 4, wherein the aqueous solution has an EDTA concentration of about 0.1 mg/ml to about 1.0 mg/ml.

6. The pharmaceutical dosage form of claim 1, wherein the acid is selected from the group consisting of citric acid, tartaric acid, ascorbic acid, dehydroascorbic acid, acetic acid, formic acid, methanoic acid, butanoic acid, ethanoic acid, benzoic acid, butyric acid, malic acid, propionic acid, epoxysuccinic acid, muconic acid, furanacrylic acid, citramalic acid, capric acid, stearic acid, caproic acid, malonic acid, succinic acid, diethylacetic acid, methylbutyric acid, hydrochloric acid, hydrobromic acid, phosphoric acid, nitric acid, and sulfuric acid.

7. The pharmaceutical dosage form of claim 6, wherein the molar concentration of the acid is about 0.15 molar to about 1.0 molar.

8. The pharmaceutical dosage form of claim 1, wherein the aqueous solution exhibits a 7 day, 4° C. carbidopa degradation rate of less than 5%.

9. A pharmaceutical composition comprising a solid formulation of levodopa, carbidopa, an acid, and a metal chelator that is soluble in an aqueous liquid and combinable with the liquid to form a solution comprising the pharmaceutical dosage form of claim 1.

10. The pharmaceutical composition of claim 9 wherein said solid formulation further comprises sodium benzoate.

11. The pharmaceutical composition of claim 9, wherein said solid formulation further comprises an artificial sweetener.

12. The pharmaceutical composition of claim 9, wherein said solid formulation further comprises hydroxypropylcellulose.

13. The pharmaceutical composition of claim 9, wherein said solid formulation further comprises citric acid.

14. The pharmaceutical composition of claim 13, wherein the solid formulation comprises a granulation binder.

15. The pharmaceutical composition of claim 14, further comprising an artificial sweetener, and sodium benzoate, and wherein the chelator comprises EDTA or a salt thereof.

16. A pharmaceutical composition kit comprising: a liquid component comprising water; and a solid component comprising levodopa and carbidopa, the solid component adapted to be dissolved in the liquid component, the combination forming a solution, the solution comprising an aqueous solution of levodopa, carbidopa, an acid, and a metal chelator, wherein the levodopa concentration is up to about 30 mg/ml, the molar ratio of levodopa to carbidopa is 3:1 to 25:1, and the solution exhibits a 7 day, 25° C. carbidopa degradation rate of less than 5%.

17. A liquid formulation comprising an aqueous solution comprising between 1 and 5 mg/ml levodopa, between 0.25 and 1.25 mg/ml carbidopa, between 3 and 10 mg/ml citric acid, and at least 0.025 µg/ml EDTA, wherein the molar ratio of levodopa to carbidopa stabilizes the carbidopa, the pH of the formulation is less than 3, and the solution exhibits a 7 day, 25° C. carbidopa degradation rate of less than 5%.

18. A pharmaceutical composition comprising a solid formulation of levodopa, carbidopa, an acid, a metal chelator, and a thioether compound that is soluble in an aqueous liquid and combinable with the liquid to form a solution comprising the liquid formulation of claim 17.

19. A liquid formulation comprising an aqueous solution comprising about 4 mg/ml levodopa, about 1 mg/ml carbidopa, between 3 and 10 mg/ml citric acid, and at least 0.025 µg/ml EDTA, wherein the pH of the formulation is less than 3, and the solution exhibits a 7 day, 25° C. carbidopa degradation rate of less than 5%.

20. A pharmaceutical composition comprising a solid formulation of levodopa, carbidopa, an acid, a metal chelator, and a thioether compound that is soluble in an aqueous liquid and combinable with the liquid to form a solution comprising the liquid formulation of claim 19.

21. A pharmaceutical composition comprising a solid formulation of levodopa, the solid formulation comprising, for each 100 mg of levodopa, about 27 mg of carbidopa, about 213 mg of citric acid monohydrate, about 12.5 mg of aspartame, about 2.5 mg of sodium benzoate, and about 2.75 mg of disodium EDTA dihydrate.

22. A pharmaceutical composition comprising an aqueous solution, the solution comprising about 4 mg/ml of levodopa, about 1 mg/ml of carbidopa, about 7.8 mg/ml of citric acid, about 0.5 mg/ml of aspartame, about 0.1 mg/ml of sodium benzoate, and about 0.1 mg/ml of Na EDTA.

23. A pharmaceutical dosage form comprising an aqueous solution of levodopa, carbidopa, an acid, a metal chelator, and a thioether compound wherein the levodopa concentration is up to about 30 mg/ml, the molar ratio of levodopa to carbidopa is 3:1 to 25:1, and the solution exhibits a 7 day, 25° C. carbidopa degradation rate of less than 5%.

* * * * *